United States Patent [19]
Cohen et al.

[11] Patent Number: 6,043,081
[45] Date of Patent: Mar. 28, 2000

[54] EXPRESSION VECTORS ENCODING RECOMBINANT PROTEINS COMPRISING A VPR/VPX VIRION INCORPORATION DOMAIN FOR TARGETING INTO HIV-1 OR HIV-2 VIRIONS

[75] Inventors: Eric A. Cohen; Dominique Bergeron; Florent Checroune; Xiao-Jian Yao; Gary Pignac-Kobinger, all of Montréal, Canada

[73] Assignee: Universite De Montreal, Montreal, Canada

[21] Appl. No.: 08/524,694

[22] Filed: Sep. 7, 1995

Related U.S. Application Data

[63] Continuation-in-part of application No. 08/301,915, Sep. 7, 1994, Pat. No. 5,861,161.

[51] Int. Cl.[7] .............................. C12N 15/00; C12N 5/00; C12N 15/63; A61K 48/00
[52] U.S. Cl. ....................... 435/320.1; 435/325; 435/440; 435/455; 514/44
[58] Field of Search ............................ 435/320.1, 69.1, 435/325, 440, 455; 514/44

[56] References Cited

U.S. PATENT DOCUMENTS 5,650,306   7/1997   Nabel et al. ......................... 435/172.3

FOREIGN PATENT DOCUMENTS

| WO 90/15875 | 12/1990 | WIPO . |
| WO 93/25235 | 12/1993 | WIPO . |
| WO 94/04686 | 3/1994 | WIPO . |
| WO 94/19456 | 9/1994 | WIPO . |
| WO 95/16705 | 6/1995 | WIPO . |

OTHER PUBLICATIONS

Kondo E. et al., 1995, Journal of Virology 69:2759–2764.
Kappes J.C. et al., 1995, Keystone Symposium on Gene Therapy and Molecular Medicine, Journal of Cellular Biochemistry Supplement, p. 395.
Wu X. et al., 1994, Journal of Virology 68:6161–6169.
Horton R. et al., 1994, Virology 199:453–457.
Orkin et al. Report and Recommendations of the panel to assess the NIH investment in research on gene therapy. Distributed by the National Institutes of Health, Dec. 7, 1995.
Levy, J. A. Pathogenesis of Human Immunodeficiency Virus Infection. Microbiological reviews, vol. 57, pp. 183–289, Mar. 1993.
Johnston et al. Present Status and Future prospects for HIV therapies. Science, vol. 260, pp. 1286–1293, May 28, 1993
Wu et al., Journal of Virology, 69(6):3389–3398, 1995.
Wu et al., American Society for Microbiology, p. 60, abstract No. 31, 1995.
Wu et al., American Society for Microbiology, p. 63, abstract No. 44, 1995.
Kappes et al., J. Cellular Biochemistry, 18B:162, abstract No. J513, 1994.
Matsuda et al., PNAS USA, 90:3544–3548, 1993.
Kim et al., AIDS Res. Hum. Retro., 8:1033–1038, 1992.
Feinberg et al., AIDS Res. Hum. Retro., 8:1013–1022, 1992.
Cohen et al., 1988, Nature, 334:532–534.
Lavallée et al., 1994, J. Virol., 68:1926–1934.

(List continued on next page.)

*Primary Examiner*—Bruce R. Campell
*Assistant Examiner*—Deborah J. R. Clark
*Attorney, Agent, or Firm*—Klauber & Jackson

[57] ABSTRACT

The present invention relates to a Vpr protein, a Vpx protein or fragments thereof which permit the development of chimeric molecules that can be specifically targeted into the mature HIV-1 and HIV-2 virions to affect their structural organization and/or functional integrity, thereby resulting in gene therapy for HIV-1 and HIV-2 infections. The present invention also relates to Vpr/Vpx protein fragments, p6 protein, p6 protein fragment, or functional derivatives thereof which interfere with the native Vpr/Vpx incorporation into HIV-1 and HIV-2 virions. The present invention also relates to treatment of HIV-1 and HIV-2 infections based on the proteins of the present invention.

72 Claims, 15 Drawing Sheets

OTHER PUBLICATIONS

Levy et al., 1993, Cell, 72:541–550.
Lu et al., 1993, Journal of Virology, 67(1):6542–6550.
Myers et al., 1993, Human Retroviruses and AIDS 1993 I–II, Los Alamos National Laboratory, New Mexico, USA.
Paxton et al., 1993, Journal of Virology, 67(12):7229–7237.
Wagner et al., 1994, Virology, 200:162–175.
Wills, 1989, Nature, 340:323–324.
Yao et al., 1992, Journal of Virology, 66(8):5119–5126.
"IUPAC–IUB Commission on Biochemical Nomenclature", Biochemistry, 1972, 11:1726–1732.
Tristem et al., 1992, EMBO J., 11:3405–12.
Yu et al., 1993, J. Virol. 67:4386–90.
Aldovini et al., Eds, 1990, Techniques in HIV Research, Stockton Press.
Morgenstern et al., 1990, Nucl. Acids Res. 18:3587–96.
Kimpton et al., 1992, J. Virol. 6:2232–39.
Wang et al., 1994, Virology, 200:524–534.
Morgan et al., 1993, Annu. Rev. Biochem., 62:191–217.
Bevec et al. (1992) Proc. Natl. Acad. Sci. USA 89:9870–4.
Boeke et al. (1996) Trends Microbiol. 4:421–7.
Checroune et al. (1995) J. AIDS Hum. Retrovirol. 10:1–7.
Fletcher et al. (1997) EMBO J. 16:5123–38.
Park et al. (1996) J. AIDS Hum. Retrovirol. 11:341–50.
Kappes et al. (1993) Virol. 193:222–33.
Lu et al. (1995) J. Virol. 69:6873–9.
Malim et al. (1992) J. Exp. Med. 176:1197–201.
Rocquigny et al. (1997) J. Biol. Chem. 272:30753–9.
Sato et al. (1996) Virol. 220:208–12.
Serio et al. (1997) Proc. Natl. Acad. Sci. USA 94:3346–51.
Woffendin et al. (1996) Proc. Natl. Acad. Sci. USA 93:2889–94.
Wu et al. (1996) J. Virol. 70:3378–84.
Wu et al. (1997) EMBO J. 16:5113–22.
Kondo et al. (1996) J. Virol. 70:159–64.

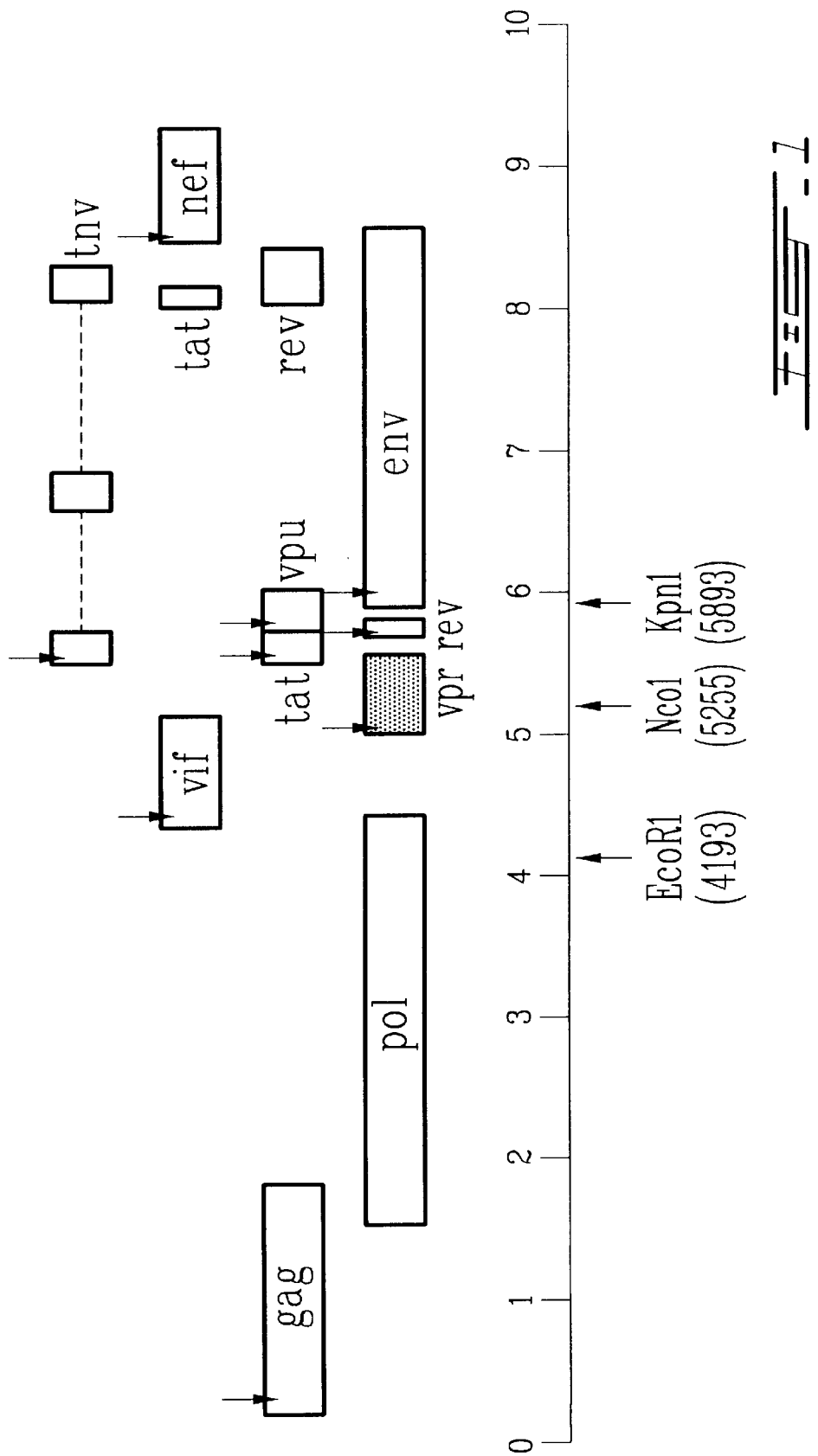

```
                          VPR from HIVLAI
Met Glu Gln Ala Pro Glu Asp Gln Gly Pro Gln Arg Glu Pro His Asn
 1               5                  10                  15
Glu Trp Thr Leu Glu Leu Leu Glu Glu Leu Lys Asn Glu Ala Val Arg
            20                  25                  30
His Phe Pro Arg Ile Trp Leu His Gly Leu Gly Gln His Ile Tyr Glu
            35                  40                  45
Thr Tyr Gly Asp Thr Trp Ala Gly Val Glu Ala Ile Ile Arg Ile Leu
    50                  55                  60
Gln Gln Leu Leu Phe Ile His Phe Arg Ile Gly Cys Arg His Ser Arg
65              70                  75                      80
Ile Gly Val Thr Gln Gln Arg Arg Ala Arg Asn Gly Ala Ser Arg Ser
            85                  90                      95
                          VPR from HIV2ROD
Met Ala Glu Ala Pro Thr Glu Leu Pro Pro Val Asp Gly Thr Pro Leu
 1               5                  10                  15
Arg Glu Pro Gly Asp Glu Trp Ile Ile Glu Ile Leu Arg Glu Ile Lys
            20                  25                  30
Glu Glu Ala Leu Lys His Phe Asp Pro Arg Leu Leu Ile Ala Leu Gly
            35                  40                  45
Lys Tyr Ile Tyr Thr Arg His Gly Asp Thr Leu Glu Gly Ala Arg Glu
    50                  55                  60
Leu Ile Lys Val Leu Gln Arg Ala Leu Phe Thr His Phe Arg Ala Gly
65              70                  75                      80
Cys Gly His Ser Arg Ile Gly Gln Thr Arg Gly Gly Asn Pro Leu Ser
            85                  90                      95
Ala Ile Pro Thr Pro Arg Asn Met Gln
            100             105
                          VPX from HIV2ROD
Met Thr Asp Pro Arg Glu Thr Val Pro Pro Gly Asn Ser Gly Glu Glu
 1               5                  10                  15
Thr Ile Gly Glu Ala Phe Ala Trp Leu Asn Arg Thr Val Glu Ala Ile
            20                  25                  30
Asn Arg Glu Ala Val Asn His Leu Pro Arg Glu Leu Ile Phe Gln Val
            35                  40                  45
Trp Gln Arg Ser Trp Arg Tyr Trp His Asp Glu Gln Gly Met Ser Glu
    50                  55                  60
Ser Tyr Thr Lys Tyr Arg Tyr Leu Cys Ile Ile Gln Lys Ala Val Tyr
65              70                  75                      80
Met His Val Arg Lys Gly Cys Thr Cys Leu Gly Arg Gly His Gly Pro
            85                  90                      95
Gly Gly Trp Arg Pro Gly Pro Pro Pro Pro Pro Pro Gly Leu Val
            100             105                 110
```

FIG. 2

```
                PREDICTED HELIX                            PREDICTED HELIX
MEQAPEDQGPQREPHNEWTLELLEELKNEAVRHFPRIWLHGLGQHIYETYGDTWAGVEAIIRILQQLLFIHFRIGCRHSRIGVTRQRRARNGASRS
         10        20        30        40        50        60        70        80        90
```

HxBRUWT
----------------------------------------------------------------------------------------------

HxBRUA30F
---------------------------F------------------------------------------------------------------

HxBRUH33I
------------------------------I---------------------------------------------------------------

HxBRUR73S
-----------------------------------------------------------------------S----------------------

HxBRUG75N
-------------------------------------------------------------------------N--------------------

HxBRUR76/79
--------------------------------------------------------------------------J---

HxBRUR77/79
---------------------------------------------------------------------------J--

HxBRUR72/78
----------------------------------------------------------------------J-----

HxBRURE12,13PG
----------PG----------------------------------------------------------------------------------

HxBRUE25K
-----------------------K----------------------------------------------------------------------

HxBRUEA29,30FK
--------------------------FK------------------------------------------------------------------

HxBRUIL63,64KR
----------------------------------------------------------------KR----------------------------

HxBRULL68,70RK
---------------------------------------------------------------------RK-----------------------

HxBRUSR,79,80ID
--------------------------------------------------------------------------ID------------------

FIG. 3

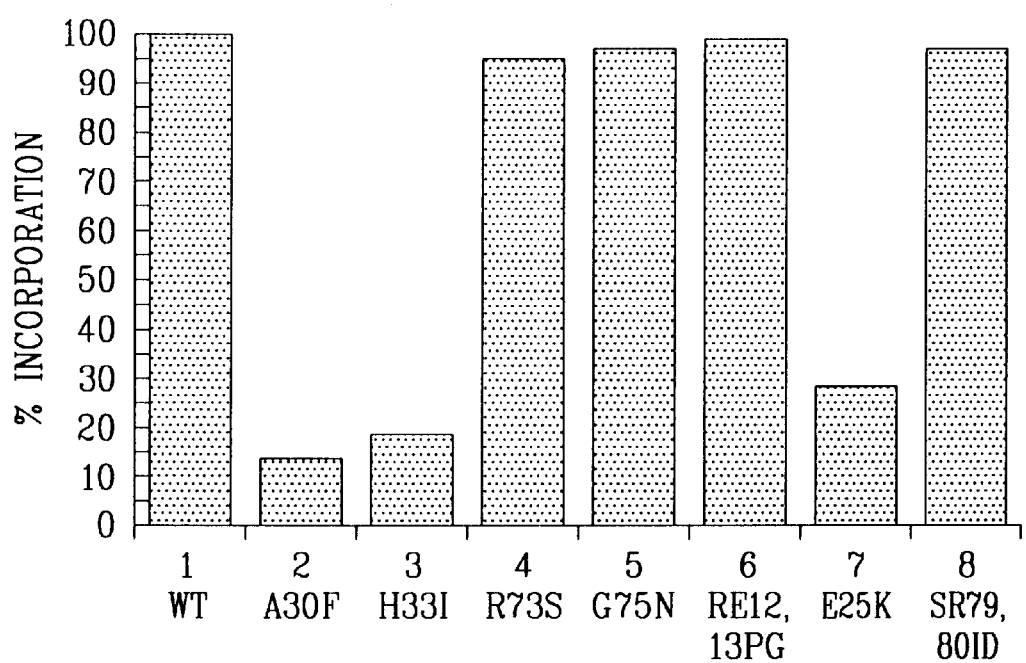

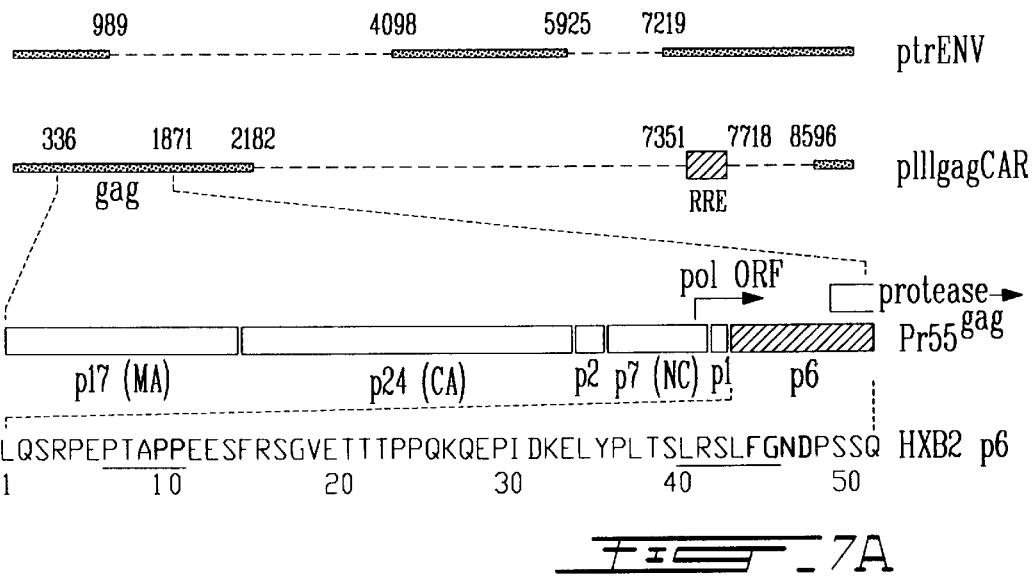
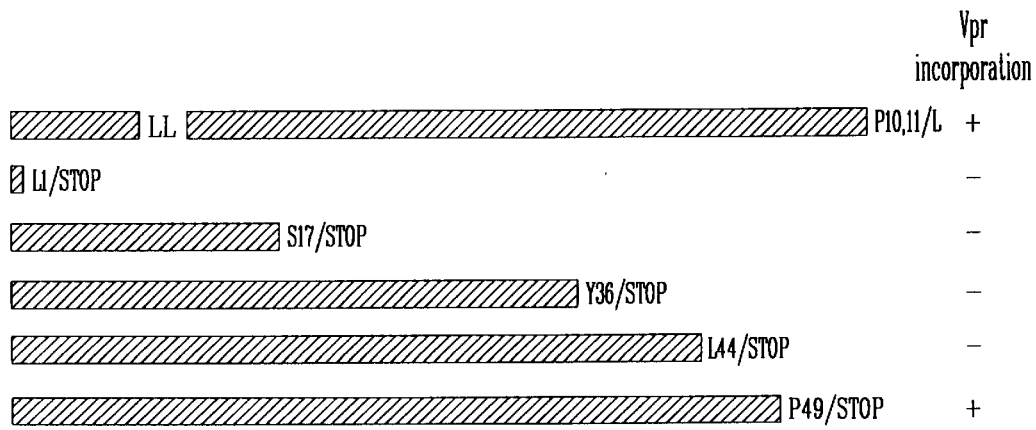

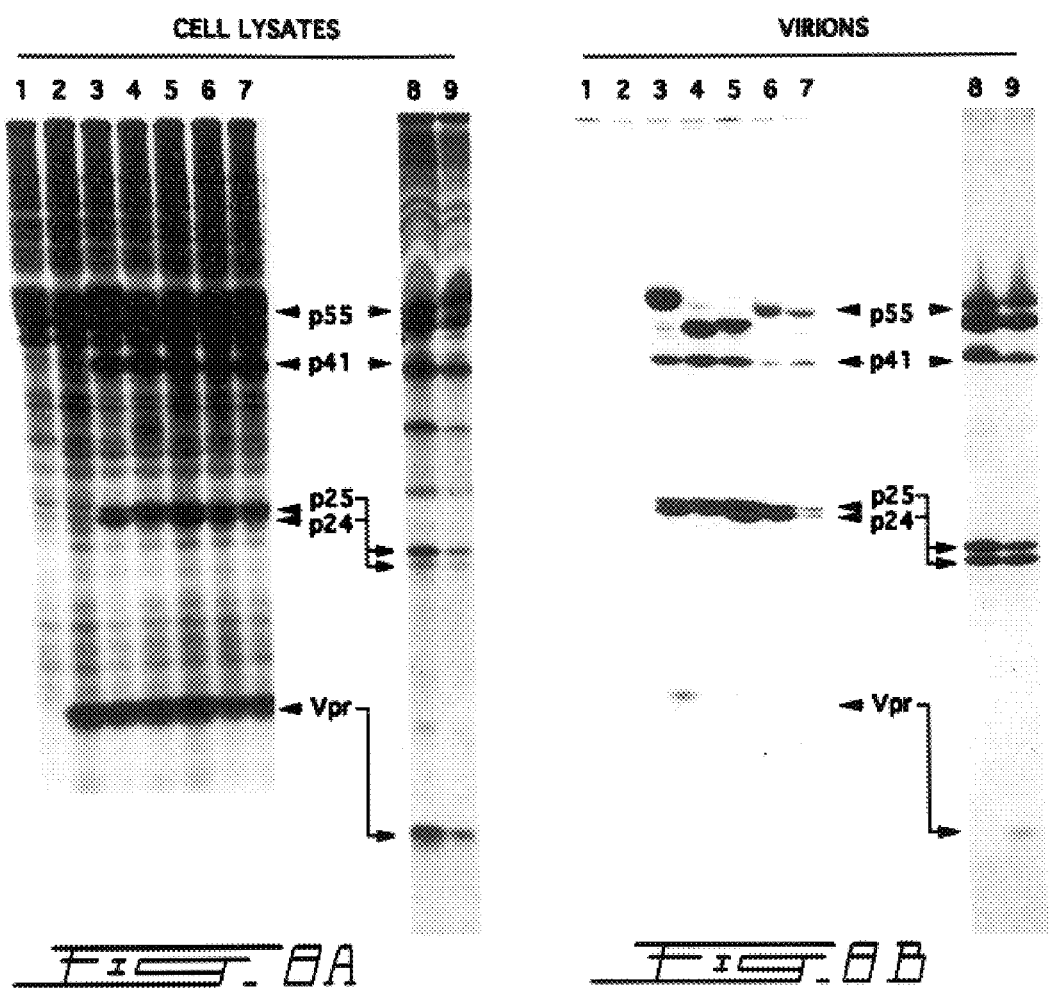

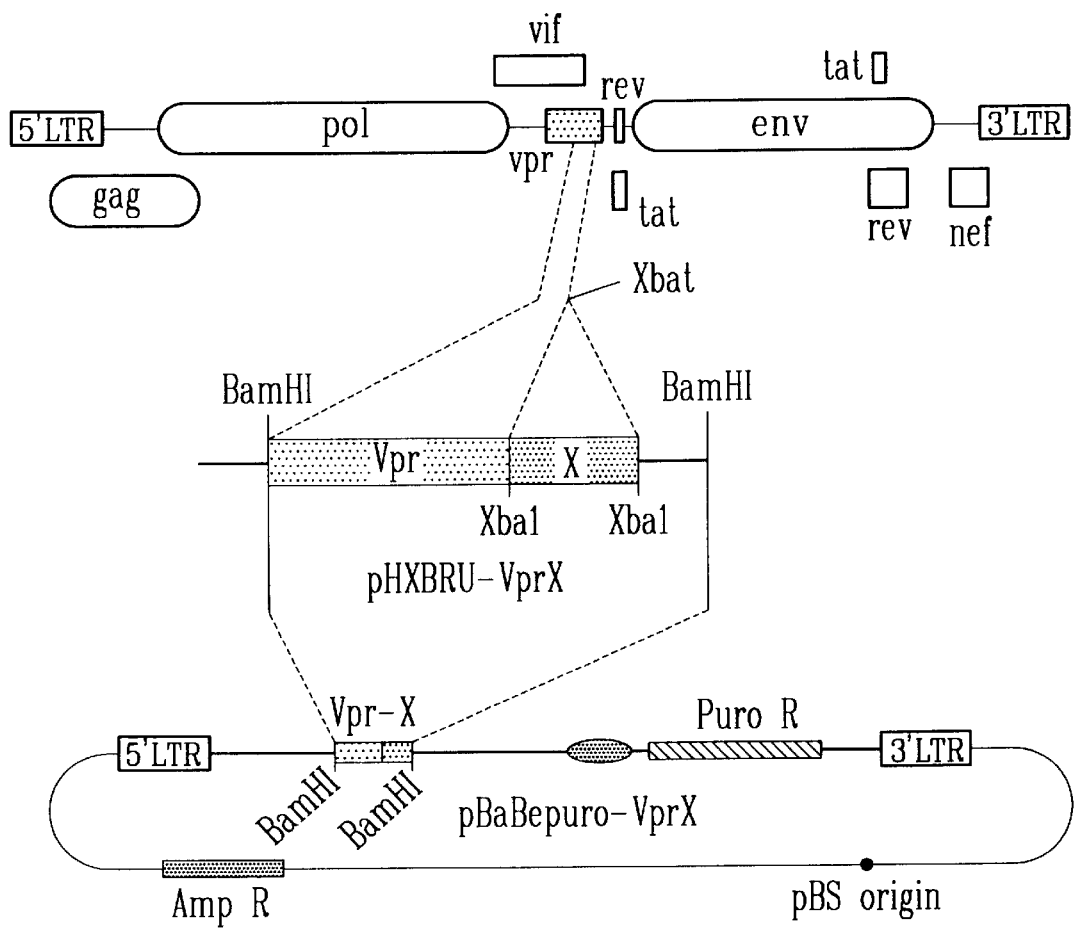

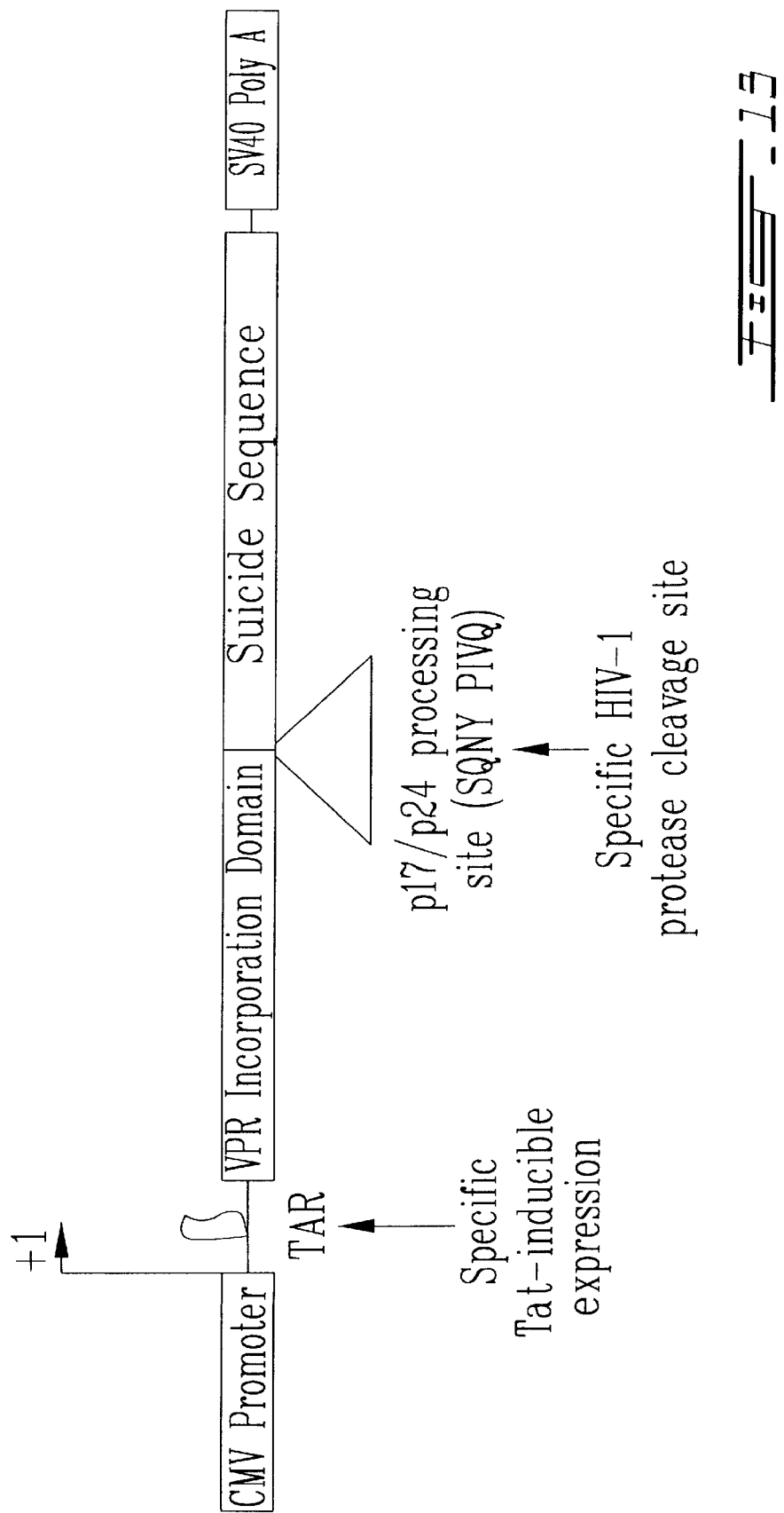

EXPRESSION VECTORS ENCODING RECOMBINANT PROTEINS COMPRISING A VPR/VPX VIRION INCORPORATION DOMAIN FOR TARGETING INTO HIV-1 OR HIV-2 VIRIONS

This application is a continuation in part of U.S. application Ser. No. 08/301,915 filed Sep. 07, 1994, U.S. Pat. No. 5,861,161, Jan. 19, 1999.

BACKGROUND OF THE INVENTION (a) Field of the Invention

The invention relates to two different approaches using the Vpr/Vpx protein or p6 protein for treatment of HIV-1 and HIV-2 infections.

(b) Description of Prior Art

Acquired Immune Deficiency Syndrome (AIDS) is a slow degenerative disease of the immune and nervous systems caused by the Human Immunodeficiency Virus (HIV). The life cycle of HIV lies at the heart of the AIDS pandemic. The spread of the disease is primarily determined by the infectious properties of this virus. Progressive lethal degeneration of the immune and central nervous systems results from long term chronic replication of this virus.

HIV belongs to a unique virus family, the retroviridae, a group of small, enveloped, positive stranded, RNA viruses (Lavallée et al., 1994, *J. Virol.*, 68:1926–1934; International Patent Application No. WO 90/158,75 on Dec. 27, 1990 in the name of DANA FARBER CANCER INSTITUTE). These viruses code for an enzyme, the reverse transcriptase (RT), which enables them to replicate their RNA genome through a DNA intermediate. Simple retroviruses contain three, contiguous reading frames coding for the gag, pol and env genes, which constitute their structural and enzymatic repertoire, all packaged in the progeny virion. The gag and env genes encode the core nucleocapsids proteins and the membrane glycoproteins of the virus, respectively, whereas the pol gene gives rise to the reverse transcriptase and other enzymatic activities (ribonuclease H, integrase and protease) that are essential for viral replication. HIV belongs to the lentivirus subfamily, members of which are characterized by several additional open reading frames (ORF) not found in simple retroviruses (FIG. 1). These ORFs all appear following gag-pol sequences, either immediately preceding the env sequences or overlapping it, and at least in one case, nef, extending well into the 3' Long Terminal Repeat (LTR). These ORFs code for non-structural viral proteins readily detectable in the cells. Much evidence has accumulated indicating that these gene products, collectively referred to as auxiliary proteins, are capable of modulating viral replication and infectivity.

HIV-1 possesses at least six such auxiliary proteins, namely, Vif, Vpr, Tat, Rev, Vpu and Nef. The closely related HIV-2 does not code for Vpu, but codes for another unrelated protein, Vpx, not found in HIV-1. Mutations affecting either Tat or Rev severely impair viral replication indicating that these two auxiliary proteins are essential for viral replication. However, at least in vitro, mutations affecting other auxiliary proteins result in minimal effect on the viral replication kinetics. Hence, these proteins have been dubbed dispensable or non-essential for in vitro replication, and are usually referred to as accessory gene products.

In the past few years, it has become evident that while these "accessory" genes are not required for productive replication, they are nonetheless capable of affecting replication events, even in vittro. More importantly, recent data indicates that they may affect pathogenesis in vivo.

The vpr gene encodes a 14 kDa protein (96 amino acids) in most strains of HIV-1 (FIG. 2; Myers et al., 1993, Human Retroviruses and AIDS 1993 I–II, Los Alamos National Laboratory, N.Mex., USA), although the open reading frame is often truncated in viral strains extensively passaged in tissue culture. The vpr open reading frame is also present in HIV-2 isolates and in most but not in all SIV isolates. A sequence similar to HIV-1 vpr is also found in Visna virus. The Vpr protein is made from a singly spliced rev-dependent mRNA species that accumulates late in infection. The Vpr protein of HIV and SIV have recently been shown to be present in mature viral particles in multiple copies. Amino acid comparison between vpx (a gene unique to HIV-2 and SIVs), and vpr from both HIV-2 and HIV-1, showed regions of strong homology (Tristem et al., 1992, EMBO J. 11: 3405–12). Like Vpr, Vpx is also packaged into the mature virion and has been shown to confer a growth advantage to viruses expressing the protein (Yu et al., 1993, J. Virol. 67: 4386–90). Interestingly, Vpx can be incorporated into HIV-1, HIV-2 or SIV with similar efficiencies. Based on the shared function, properties, including viral compartimentalization, and homologies of sequences between Vpr and Vpx, vpx in the HIV-2/SIV group, is thought to have arisen by duplication of the vpr gene (FIG. 2; Tristem et al., 1992, EMBO J. 11: 3405–12; and Myers et al., 1993, Human Retroviruses and AIDS 1993 I–II, Los Alamos National Laboratory, New Mexico, USA). Interestingly, Vpr and Vpx are the first regulatory protein of any retrovirus found to be associated with viral particles. Other regulatory proteins, such as tat, Rev, Nef, Vif and Vpu are not virion-associated. The assembly and maturation of HIV-1 viral particles is a complex process in which the structural Gag, Pol and Env gene products are expressed in the form of polyprotein precursors. The Gag proteins of HIV play a central role in virion assembly and budding. Gag proteins are initially synthesized as myristylated polyprotein precursors, $Pr55^{gag}$ and $Pr160^{gag-pol}$, which are transported to the inner face of the plasma membrane where they can direct particle formation, even in the absence of other viral proteins. Complete budding leads to formation of immature particles, followed by HIV protease mediated cleavage of the Gag and Gag-Pol precursor polyproteins and formation of mature HIV particles with condensed core. The mature virion proteins derived from cleavage of the gag-encoded precursor, $Pr55^{gag}$, include the p17 matrix protein (MA), the p24 capsid protein (CA), the p7 nucleocapsid protein (NC), and a small proline-rich peptide of approximately 6 kDa designated p6 which are linked in this order in the polyprotein precursor. Vpr is not part of the virus polyprotein precursors and its incorporation occurs by way of an interaction with a component normally found in the viral particle. It was recently reported that the HIV-1 Vpr could be incorporated in trans into viral-like particle (VLP) originating from expression of the $Pr55^{gag}$ only (Lavallée et al., 1994, J. Virol., 68:1926–1934). Data from this and other studies indicate that Vpr incorporation appeared to result from a direct interaction of Vpr with the carboxy-terminal region of the $Pr55^{gag}$ polyprotein (Paxton et al., 1993, J. Virol., 67(12):7229–7237; Lu et al., 1993, J. Virol., 67(1) :6542–6550).

Functional studies indicated that the full length vpr protein could confer favorable growth properties to viruses. The increase in virion production is more pronounced in primary macrophages in both HIV-1 and HIV-2 systems, suggesting that Vpr function may be important in specific target cells. Interestingly, while mutations affecting HIV-1 vpr do not affect replication in peripheral blood mononuclear cells (PBMC), mutations in HIV-2 vpr results in a measurable impairment in these cells. Similarly, a recent study using anti-sense RNA directed against vpr inhibited viral replication in primary macrophages but not in transformed T-cells. Previous work indicated that this rapid growth advantage may be conferred by the weak transactivation property of Vpr on HIV-LTR directed gene expression (European Patent Application published under No. 474,797 on Mar. 18, 1992 in the name of DANA FARBER CANCER INSTITUTE). Cotransfection experiments suggest that vpr could augment the expression of a reporter gene from several heterologous promoters by approximately three to ten fold.

The carboxyl terminal sequence of Vpr have been shown to be important for Vpr mediated transactivation as prematurely truncated proteins are non-functional and are not packaged into the virion. Interestingly, a recent report also indicated that the carboxyl terminal of the protein is important for nuclear localization (Lu et al., 1993, J. Virol., 67(1):6542–6550). A specific vpr responsive LTR sequence was not identified and the exact mechanism by which vpr augments reporter gene expression is not clear. The precise mode of action of vpr is yet to be established. However, the presence of Vpr in the viral particle (a property also shared by Vpx) suggests that this protein has a role in the early stage of infection. Virion-associated non-structural proteins in many viral systems play a pivotal enzymatic functions in early replication steps, either because cellular homologues are unavailable or are sequestered, for example, in the nucleus. It is possible that Vpr is one such protein, capable of modulating early viral specific functions such as reverse transcription stabilization of early RNA or DNA intermediates, transport to the nucleus or integration. It is equally possible that Vpr could function at an early step, in a non-viral specific manner, by triggering processes that could make the cellular environment congenial to establish viral infection. In this regard, HIV-1 Vpr has been reported to be involved in inducing cellular differentiation in rhabdomyosarcoma cells (Levy et al., 1993, Cell, 72:541–550). Finally, because Vpr is synthesized late in the infection cycle of HIV, it may regulate the morphogenesis of the virus (late events) by an unknown mechanism or constitute a structural protein involved in the integrity of the virions.

The use of transport polypeptides for biological targeting is well known and was adapted to many fields. The HIV Tat protein has been described to effect the delivery of molecules into the cytoplasm and nuclei of cells (International Application published on Mar. 3, 1994 as No. WO 94/04686 in the name of BIOGEN, INC.). However, the Tat transport polypeptides can not allow the delivery of molecules to HIV virions. Viral proteins such as Gag of Rous sarcoma virus and Moloney murine leukemia virus and portion of HIV-1 Gag protein have been used as carrier for incorporation of foreign antigens and enzymatic markers into retroviral particles (Wang et al., 1994, Virology, 200:524–534). However, most of the Gag protein sequences are essential for efficient viral particles assembly, thus limiting the use of such virion components as carrier.

It would be highly desirable to be provided with means to target molecules to mature HIV-1 and HIV-2 virions to affect their structural organization and/or functional integrity.

It would also be highly desirable to be provided with a Vpr protein, a Vpx protein or fragments thereof which permit the development of chimeric molecules that can be specifically targeted into the mature HIV-1 and HIV-2 virions to affect their structural organization and/or functional integrity, thereby resulting in treatment of HIV-1 and HIV-2 infections.

It would also be highly desirable to be provided with a therapeutic agent which permit the targeting of chimeric molecules into the mature HIV-1 and HIV-2 virions as a treatment for HIV-1 and HIV-2 infections.

It would also be highly desirable to be provided with the identification of the protein interactions responsible for Vpr or Vpx incorporation into the mature HIV-1 and HIV-2 virions.

It would also be highly desirable to be provided with means to incorporate Vpr or Vpx into the mature HIV-1 and HIV-2 virions by making use of the protein interactions responsible for incorporation of Vpr or Vpx therein, thereby affecting the functional integrity of the HIV virions.

It would also be highly desirable to be provided with a Vpr protein fragment, a Vpx protein fragment, a p6 protein or p6 protein fragment which permits the development of molecules that can specifically interfere with the protein interactions responsible for Vpr or Vpx incorporation into the mature HIV-1 and HIV-2 virions to affect their functional integrity, thereby resulting in treatment of HIV-1 and HIV-2 infections.

It would also be highly desirable to be provided with a therapeutic agent which interferes with the protein interaction responsible for Vpr or Vpx incorporation in the mature HIV-1 and HIV-2 virions as a treatment for HIV-1 and HIV-2 infections.

SUMMARY OF THE INVENTION

One aim of the present invention is to provide means to target molecules to mature HIV-1 and HIV-2 virions to affect their structural organization and/or functional integrity Another aim of the present invention is to provide a Vpr protein, a Vpx protein or fragments thereof which permit the development of chimeric molecules that can be specifically targeted into the mature HIV-1 and HIV-2 virions to affect their structural organization and/or functional integrity, thereby resulting in treatment of HIV-1 and HIV-2 infections.

Another aim of the present invention is to provide a therapeutic agent which permits the targeting of chimeric molecules into the mature HIV-1 and HIV-2 virions as a treatment for HIV-1 and HIV-2 infections.

Another aim of the present invention is to provide the identification of the protein interactions responsible for Vpr or Vpx incorporation into the mature HIV-1 and HIV-2 virions.

Another aim of the present invention is to provide means to incorporate Vpr or Vpx into the mature HIV-1 and HIV-2 virions by making use of the protein interactions responsible for incorporation of Vpr or Vpx therein, thereby affecting the functional integrity of the HIV virions.

Another aim of the present invention is to provide a Vpr protein fragment, a Vpx protein fragment, a p6 protein or p6 protein fragment which permit the development of molecules that can specifically interfere with the protein interactions responsible for Vpr or Vpx incorporation into the mature HIV-1 and HIV-2 virions to affect their functional integrity, thereby resulting in treatment of HIV-1 and HIV-2 infections.

Another aim of the present invention is to provide a therapeutic agent which interferes with the protein interactions responsible for Vpr or Vpx incorporation into the mature HIV-1 and HIV-2 virions as a treatment for HIV-1 and HIV-2 infections.

In accordance with the present invention there is provided a protein for targeting into a mature HIV-1 or HIV-2 virion, which comprises a sufficient number of amino acids of a Vpr protein, a Vpx protein, functional derivatives or fragments thereof, wherein the protein interacts with a Gag-precursor protein of the mature virion and is incorporated by the virion. More specifically, the protein interacts with the protein p6 which is a component of the Gag-precursor protein.

More specifically, the protein of the present invention, further comprises a protein fragment covalently attached to its N- or C-terminal to form a chimeric protein which is also incorporated by the mature virion. Such an attached protein fragment of the present invention consists of amino acid sequence effective in reducing HIV expression or replication, the amino acid sequence encoding for example a RNase activity, protease activity, creating steric hindrance during virion assembly and morphogenesis and/or affecting viral protein interactions responsible for infectivity and/or viral replication.

More specifically, the protein of the present invention, further comprises a molecule to form a protein-molecule complex which is also incorporated by the mature virion. Such a molecule is selected from the group consisting of anti-viral agents, RNases, proteases, and amino acid sequences capable of creating steric hindrance during virion assembly and morphogenesis. The molecule of the protein-molecule complex of the present invention affects the structural organization or functional integrity of the mature virion by steric hindrance or enzymatic disturbance of the virion.

In accordance with the present invention there is also provided a protein which interferes with Vpr or Vpx incorporation into HIV-1 and HIV-2 virions and which comprises a sufficient number of amino acids of a Vpr protein fragment, a Vpx protein fragment, a p6 protein, p6 protein fragment, or its functional derivative thereof, wherein the protein interacts either with a Gag-precursor or with Vpr or Vpx protein to compete with the Vpr-Gag-precursor or Vpx-Gag-precursor interaction and consequently to interfere with the incorporation of the native Vpr or Vpx into the virions and to substantially prevent replication of the mature virion.

In accordance with the present invention there is also provided a method of substantially reducing HIV expression or replication in a patient infected with HIV-1 or HIV-2, which comprises administering at least one therapeutic agent selected from the group consisting of the protein or DNA sequences encoding the protein of the present invention, to the patient in association with a pharmaceutically acceptable carrier. The administration step of the method is effected intracellularly for anti-viral treatment including gene therapy or intracellular immunization of the patient through DNA transfection or administration of the chimeric protein. The anti-viral treatment can be effected through transfection of a patient's hematopoietic cells with a DNA construct harboring a Vpr/Vpx chimeric protein, followed by readministration of the transfected cells, and/or through administration of a DNA construct harboring a Vpr/Vpx chimeric protein or directly by administration of a Vpr/Vpx chimeric protein, via the blood stream or otherwise.

In accordance with the present invention there is also provided A vector comprising: (a)a DNA segment encoding a protein which interferes with the incorporation of native Vpr/Vpx into HIV-1 and/or HIV-2 virions, comprising a sufficient number of amino acids of a Vpr protein, a Vpx protein, a p6 protein, functional derivatives or fragments thereof; and(b)a promoter upstream of the DNA segment.

Accordingly, in view of two different approaches of the present invention, therapeutic agents which may be used in accordance with the present invention are selected from the group consisting of a protein of the present invention including Vpr/Vpx chimeras comprising RNases, proteases or amino acids sequences capable of creating steric hindrance during virion morphogenesis, and/or affecting viral protein interactions responsible for infectivity and/or viral replication, Vpr/Vpx protein fragment, p6 protein and p6 protein fragment, and DNA sequences encoding a protein of the present invention.

In accordance with the present invention there is also provided a pharmaceutical composition for reducing HIV expression in a patient infected with HIV-1 or HIV-2, which comprises a sufficient amount of the therapeutic agent of the present invention in association with a pharmaceutically acceptable carrier.

BRIEF DESCRIPTION OF THE DRAWINGS

FIG. 1 shows the HIV genetic organization, where the vpr gene is positioned in the central region;

FIG. 2 shows the amino acid sequences of native Vpr protein from HIVLAI isolate and native Vpr and Vpx proteins from HIV2ROD isolate;

FIG. 3 shows the mutagenesis chart of the vpr gene of HxBH10 or pHxBRU template of HIV-1;

FIG. 6 shows quantification of the incorporation of different mutated Vpr into HIV-1 virions;

FIGS. 7A and 7B show the expression plasmids and the P6 construct plasmid expressing P6 mutant;

FIG. 8(A–B) shows the incorporation of Vpr into virions in the presence of different truncated or mutated Gag P6 protein;

FIG. 9 shows the construction of a retroviral vector (pBaBepuro) for the expression of a chimeric protein between Vpr (from HIV-1 LAI strain) and a portion of a predetermined protein (pBaBepuro-VprX), such as HIV-1 Vpu protein (pBaBepuro-VprIE) or CAT (pBaBepuro-VprCAT);

FIG. 13 shows an expression construct for the specific expression of a Vpr-based chimeric protein in HIV-infected cells.

DETAILED DESCRIPTION OF THE INVENTION

Figures 4A, 4B:
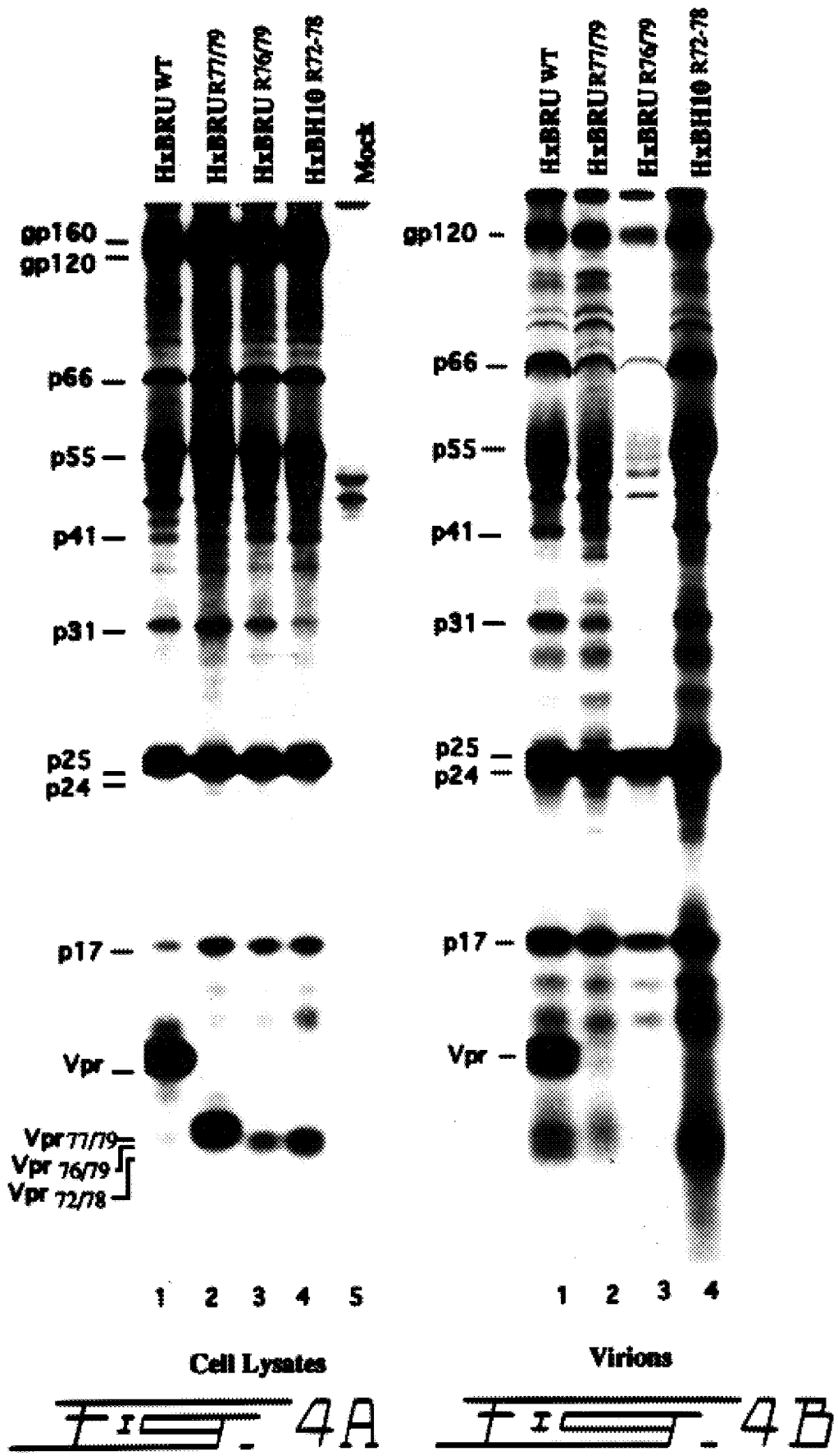
FIGS. 4(A–E) show the analysis of Vpr present in lysates and supernatants of MT4 cells infected with HIV-1 containing various mutated or truncated vpr mutants.

In accordance with the present invention, two different approaches using the Vpr/Vpx protein and p6 protein are described herein for the treatment of HIV-1 and HIV-2 infections.

In the first approach, the region of Vpr/Vpx protein, which is involved in the protein interaction responsible for Vpr/Vpx virion-incorporation, is used as a carrier to target molecules to mature HIV-1 and HIV-2 virions.

In the second approach, the region of Vpr/Vpx protein or alternatively the region of Gag-precursor, which are both involved in the protein interaction responsible for Vpr/Vpx virion-incorporation, is used to interfere with the native viral Vpr/Vpx protein incorporation.

In general, the abbreviations used herein for designating the amino acids are based on recommendations of the IUPAC-IUB Commission on Biochemical Nomenclature (Biochemistry, 1972, 11:1726–1732).

From the specification and appended claims, the term therapeutic agent should be taken in a broad sense so as to also include a combination of at least two such therapeutic agents. Further, the DNA segments or proteins according to the present invention can be introduced into individuals in a number of ways. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, which can be designed to be targeted to a specific cell type, and engineered to be administered through different routes.

In accordance with the first approach of the present invention, there is provided the use of the Vpr or Vpx protein, which is referred to as the "Vpr/Vpx" protein, functional derivatives or fragments thereof for the targeting of molecules to the HIV-1 and/or HIV-2 virions. The sequence responsible for such targeting is termed herein the Vpr/Vpx incorporation domain.

The preferred Vpr/Vpx protein, which is used in accordance with the first approach of the present invention, contains a sufficient number of amino acids corresponding to at least one of the following amino acid sequences consisting of:

```
Met Glu Gln Ala Pro Glu Asp Gln Gly Pro Gln Arg Glu Pro His Asn        (SEQ ID NO:1)
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
            35                  40                  45

Thr Tyr Gly Asp Thr Trp Ala Gly Val Glu Ala Ile Ile Arg Ile Leu
        50                  55                  60

Gln Gln Leu Leu Phe Ile His Phe Arg Ile Gly Cys Arg His Ser Arg
65                  70                  75                  80

Ile Gly Val Thr Gln Gln Arg Arg Ala Arg Asn Gly Ala Ser Arg Ser;
                85                  90                  95

Met Ala Glu Ala Pro Thr Glu Leu Pro Pro Val Asp Gly Thr Pro Leu        (SEQ ID NO:2)
1               5                   10                  15

Arg Glu Pro Gly Asp Glu Trp Ile Ile Glu Ile Leu Arg Glu Ile Lys
            20                  25                  30

Glu Glu Ala Leu Lys His Phe Asp Pro Arg Leu Leu Ile Ala Leu Gly
            35                  40                  45

Lys Tyr Ile Tyr Thr Arg His Gly Asp Thr Leu Glu Gly Ala Arg Glu
        50                  55                  60

Leu Ile Lys Val Leu Gln Arg Ala Leu Phe Thr His Phe Arg Ala Gly
65                  70                  75                  80

Cys Gly His Ser Arg Ile Gly Gln Thr Arg Gly Gly Asn Pro Leu Ser
                85                  90                  95

Ala Ile Pro Thr Pro Arg Asn Met Gln; and
            100                 105

Met Thr Asp Pro Arg Glu Thr Val Pro Pro Gly Asn Ser Gly Glu Glu        (SEQ ID NO:3)
1               5                   10                  15

Thr Ile Gly Glu Ala Phe Ala Trp Leu Asn Arg Thr Val Glu Ala Ile
            20                  25                  30

Asn Arg Glu Ala Val Asn His Leu Pro Arg Glu Leu Ile Phe Gln Val
            35                  40                  45

Trp Gln Arg Ser Trp Arg Tyr Trp His Asp Glu Gln Gly Met Ser Glu
        50                  55                  60

Ser Tyr Thr Lys Tyr Arg Tyr Leu Cys Ile Ile Gln Lys Ala Val Tyr
65                  70                  75                  80

Met His Val Arg Lys Gly Cys Thr Cys Leu Gly Arg Gly His Gly Pro
```

-continued

```
                85                  90                  95
    Gly Gly Trp Arg Pro Gly Pro Pro Pro Pro Pro Pro Gly Leu Val;
                    100                 105                 110
``` functional fragments or derivatives thereof, wherein the Vpr/Vpx protein, its fragments or derivatives thereof have retained the virion-incorporation function of the native Vpr/Vpx protein.

The expression "functional fragments or derivatives" when used herein is intended to mean any substitutions, deletions and/or additions of amino acids that do not affect the virion-incorporation function of the Vpr/Vpx native protein.

In accordance with the first approach of the present invention, a preferred Vpr/Vpx chimeric protein comprises an amino acid sequence of a Vpr/Vpx protein or a functional derivative thereof and a molecule attached to the amino acid sequence. Said molecule may be covalently attached at the N- or C-terminal of the amino acid sequence or it may be attached to the amino acid sequence at any amino acid position by chemical cross-linking or by genetic fusion.

A preferred molecule used in accordance with the present invention may be selected from the group consisting of an derivatives thereof which interfere with the native Vpr/Vpx incorporation into HIV-1 and/or HIV-2 virions. Again, the Vpr/Vpx protein fragments, p6 protein, p6 protein fragments, or functional derivatives thereof have retained their ability to interact with the native Vpr/Vpx or p6 protein, respectively. The expression "functional derivatives" when used herein is intended to mean any substitutions, deletions and/or additions of amino acids that do not destroy the functionality of the Vpr/Vpx incorporation domain or the region of the p6 protein which interacts therewith.

The preferred Vpr/Vpx protein fragments which is used in accordance with the second approach of the present invention is a fragment of the following amino acid sequence consisting of:

```
Met Glu Gln Ala Pro Glu Asp Gln Gly Pro Gln Arg Glu Pro His Asn        (SEQ ID NO:4)
1               5                   10                  15

Glu Trp Thr Leu Glu Leu Leu Glu Glu Leu Lys Asn Glu Ala Val Arg
                20                  25                  30

His Phe Pro Arg Ile Trp Leu His Gly Leu Gly Gln His Ile Tyr Glu
            35                  40                  45

Thr Tyr Gly Asp Thr Trp Ala Gly Val Glu Ala Ile Ile Arg Ile Leu
    50                  55                  60

Gln Gln Leu Leu Phe Ile His Phe
65                  70
``` anti-viral agent and/or a second amino acid sequence which contains a sufficient number of amino acids corresponding to RNases, proteases, or any protein capable of creating steric hindrance during virion morphogenesis and/or affecting viral protein interactions responsible for infectivity and/or viral replication.

wherein said fragment is a region of the Vpr/Vpx protein which binds to a Gag-precursor.

The preferred p6 protein which is used in accordance with the second approach of the present invention contains a sufficient number of amino acids corresponding to the following amino acid sequences consisting of:

```
Leu Gln Arg Ser Pro Glu Pro Thr Ala Pro Pro Glu Glu Ser Phe Arg        (SEQ ID NO:5)
1               5                   10                  15

Ser Gly Val Glu Thr Thr Thr Pro Pro Gln Lys Gln Glu Pro Ile Asp
                20                  25                  30

Lys Glu Leu Tyr Pro Leu Thr Ser Leu Arg Ser Leu Phe Gly Asn Asp
            35                  40                  45

Pro Ser Ser Gln.
    50
```

The Vpr/Vpx chimeric protein in accordance with the first approach of the present invention may be used for the targeting of molecules into the mature virions of HIV-1 and/or HIV-2, such as polypeptides, proteins and anti-viral agents, among others.

In accordance with the second approach of the present invention, there is provided the use of Vpr/Vpx protein fragments, p6 protein, p6 protein fragment, or functional The Vpr/Vpx fragment, p6 protein and p6 protein fragment in accordance with the second approach of the present invention may be used for interfering with the virion-incorporation of native Vpr/Vpx into HIV-1 and/or HIV-2 virions.

The purpose of the treatment in accordance with the first and second approaches of the present invention may be a prevention or a treatment. The product in these treatment procedures may be expressed intracellularly or provided to the cell via the blood stream.

In accordance with the first approach of the present invention, the expressed or administered product may be effective in the production of defective viral particles, for instance, viral particles with Vpr/Vpx chimeric proteins such as the ones associated with virally directed protease or nuclease or with a portion of protein which affects the structural organization and/or functional integrity of the virions.

The treatment in accordance with the second approach of the present invention may consists in the production of viral particles having substantially reduced replication capacity, for instance, HIV-1 and HIV-2 viral particles devoid of functional level of Vpr/Vpx protein as a consequence of Vpr-Gag-precursor or Vpx-Gag-precursor interaction interference using Vpr/Vpx protein fragments, p6 protein and p6 protein fragments.

HIV-1 Vpr Regions Associated with Viral Particles Incorporation

The substitution mutations and deletions of vpr were generated by site-directed mutagenesis. Wildtype vpr sequence and location of predicted alpha-helix structures are indicated at the top of FIG. 3. Oligonucleotide-directed mutagenesis of the vpr gene was carried out on DNA fragments derived from the pHxBRU template (FIG. 3) and then cloned into an infectious provirus (pHxBRU) (Lavallée et al., 1994, J. Virol., 68:1926–1934). Amino acid substitutions are indicated. BRUR 77/79, BRUR 76/79 and HxBH10 72/78 (Yao et al., 1992, J. Virol. 66:5119–5126) are truncated vpr proteins with additional unrelated amino acids generated by frame shift mutations.

Figure 4C:
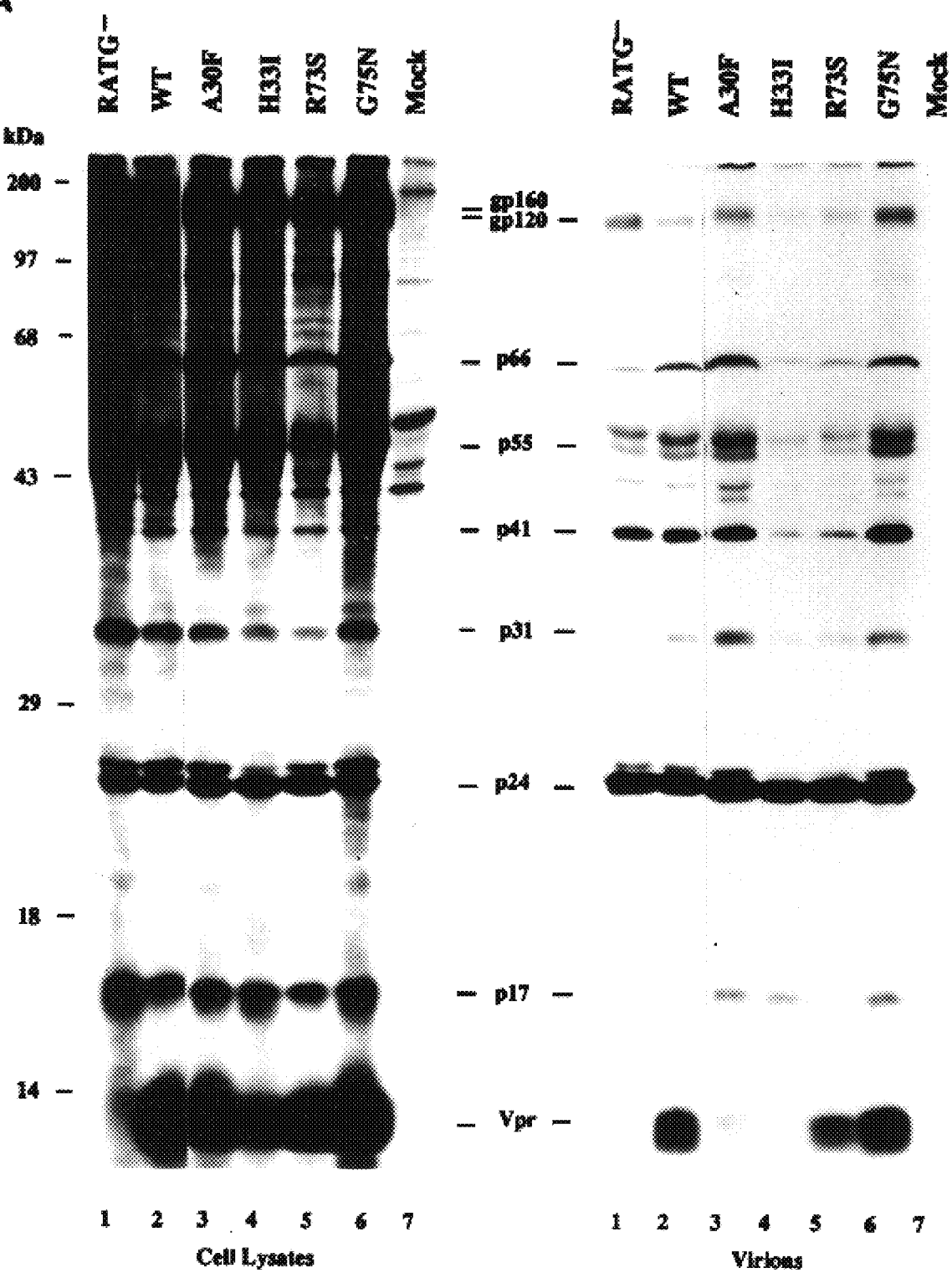
Figures 4D, 4E:
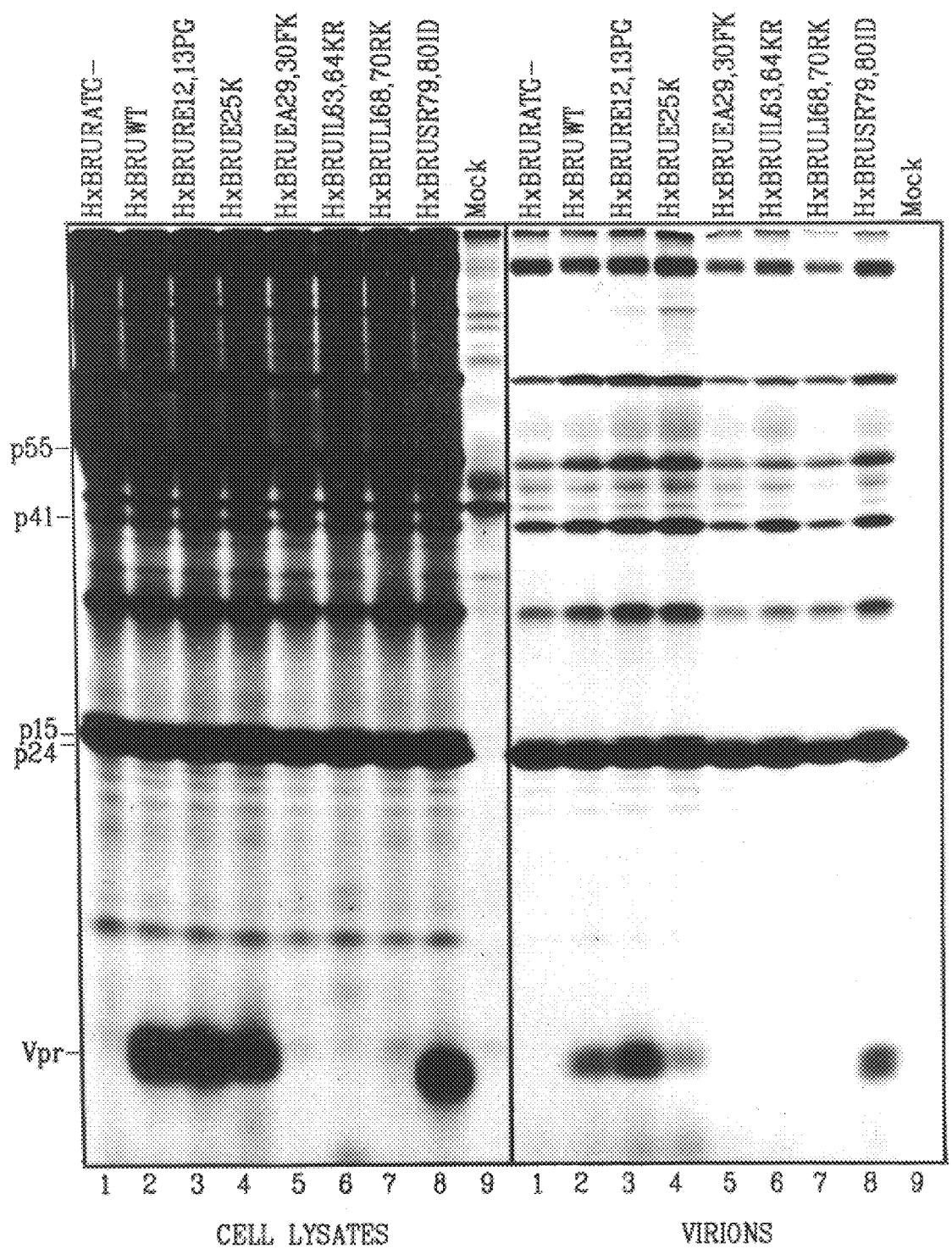

FIGS. 4A, 4B and 4C are autoradiograms that illustrate the analysis of truncated or substituted Vpr mutants in HIV-1 infected MT4 cells. $2 \times 10^6$ T-lymphoid cells (MT4) were infected (or transfected, FIG. 4C) with HIV-1 which contain wildtype or truncated Vpr (FIG. 3), as shown at the top of the autoradiograms. The position of HIV-1 viral proteins are indicated at the left of the autoradiograms (Vpr). At 40 h post-transfection, cells were labelled with 100 $\mu$Ci of $^{35}$S-methionine and 100 $\mu$Ci of $^3$H-leucine for 16 h. Virions were pelleted from cell-free supernatants by ultracentrifugation at 35,000 rpm through a 20% sucrose cushion for 2 h. Both cells (left panel) and sucrose cushion pelleted viruses (right panel, FIGS. 4A, 4B & 4C) were lyzed in RIPA buffer (140 mM NaCl, 8 mM NaHPO$_4$, 2 mM NaH$_2$PO$_4$, 1% Nonidet™ P-40, 0.5% sodium deoxycholate, 0.05% SDS) and immunoprecipitated with a HIV-1 positive human serum combined with a rabbit anti-Vpr serum. Proteins were then analyzed on a sodium dodecyl sulfate (SDS) 12.5%–17% gradient polyacrylamide gel electrophoresis (PAGE) and autoradiography. Quantification of virion associated Vpr and protein stability was determined by densitometric scanning of the autoradiograms using a laser densitometer (Molecular Dynamics™ densitometer).

Figures 5A, 5B:
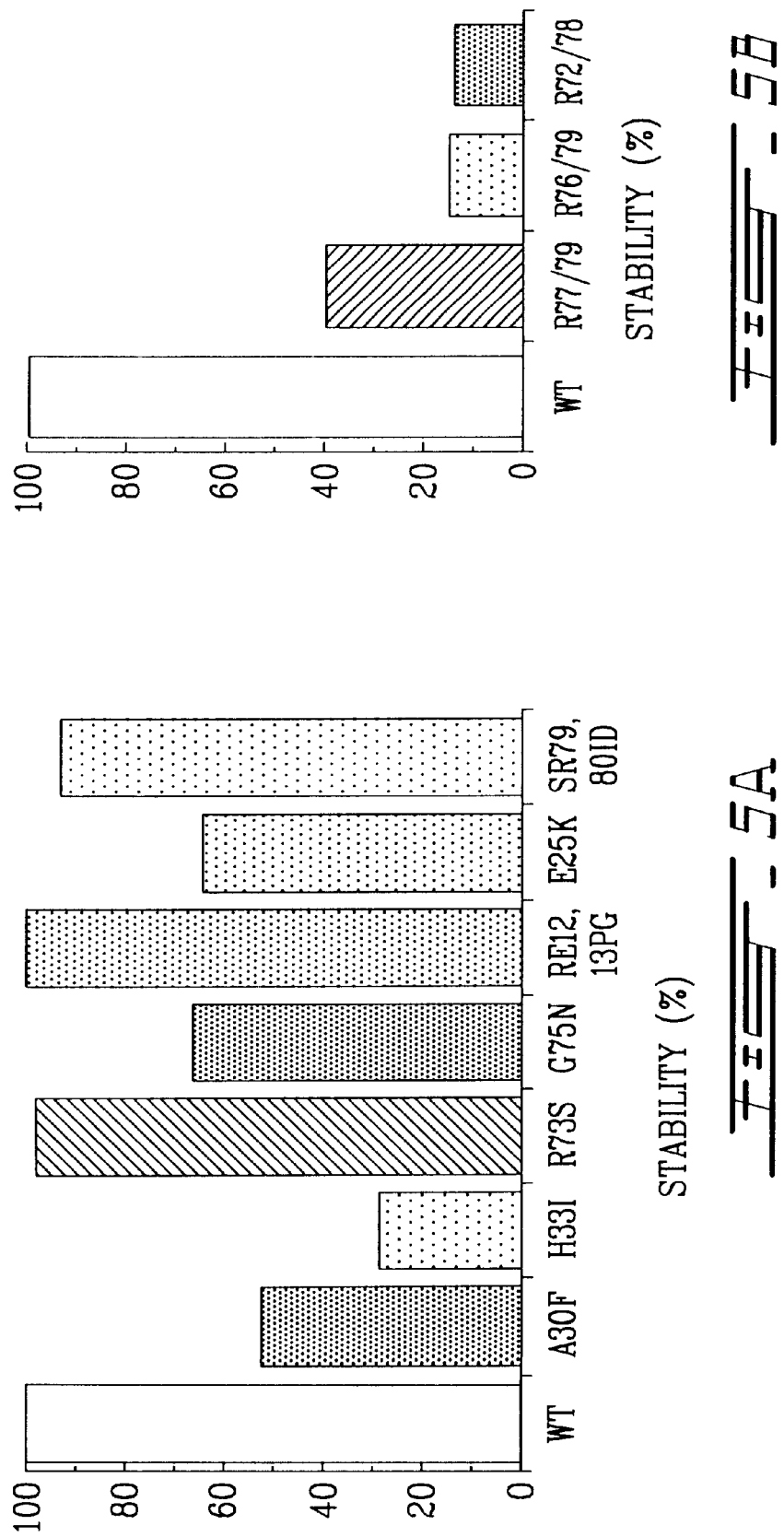
FIG. 5(A–B) shows the stability of the truncated or mutated Vpr protein in infected MT4 cells.

FIG. 5 shows the stability of different truncated (FIG. 5B) or substituted (FIG. 5A) Vpr mutants in HIV-1 infected cell lysates. The intensity of wildtype or mutated Vpr proteins were quantified relative to the intensity of the p66 reverse transcriptase (RT) bands. Immunoprecipitation analysis has shown that all truncated Vpr proteins were present at low level in cell lysates suggesting the importance of the C-terminal region for Vpr stability (FIGS. 4A and 5B).

FIG. 6 shows the efficiency of incorporation of different mutated Vpr into HIV-1 virions. The incorporation of mutated Vpr into virions was also evaluated by densitometric analysis. The intensity of Vpr proteins into virions were quantified relative to the intensity of the p66 reverse transcriptase (RT) bands in autoradiograms presented in FIGS. 4B and 4C. The results of the present invention demonstrate that substitution mutations (A30F, H331 and E25K) in the N-terminal portion of Vpr significantly impair the incorporation of Vpr protein into virions (FIGS. 4B, 4C and 6). It should be noted that this region of the protein is predicted to form an alpha helix and thus is reminiscent of a structure involved in protein-protein interaction. Interestingly, an alpha helix is also predicted from the corresponding region of Vpx. These data indicate that the N-terminus of Vpr is important for Vpr incorporation in the virion. This region will be further defined by analyzing additional Vpr mutants for their stability and virion-incorporation capacity.

HIV-1 GAG P6 Regions Associated with Vpr Incorporation

To investigate the mechanism of incorporation of Vpr, the ability of Gag-expressor plasmids, harboring deletions or mutations in the C-terminus of the capsid precursor, to target Vpr into virions in transiently transfected cells was tested. In this system two expressor plasmids described in FIG. 7A were cotransfected into COS-7 cells (Lavallée et al., 1994, J. Virol., 68:1926–1934; FIG. 7A). Deletions are shown as dotted lines between the thick lines. ptrENV contains 3109 (nucleotides 989 to 4098) and 1294 (nucleotides 5925 to 7219) base pair deletions affecting respectively gag, pol and the gp120 domain of env genes. ptrENV encodes Vpr as well as all HIV-1 auxilliary proteins (Vif, Tat, Rev, Vpu Nef and gp41). The pIIIgagCAR plasmid, a rev-dependent Gag expressor, which encodes Pr55$^{gag}$ and the protease domain of the pol gene (PR), contains the Rev-responsive element (RRE/CAR) sequence. P6 is the C-terminal components of the Pr55$^{gag}$ precursor (FIG. 7A). FIG. 7B illustrates the P6 constructs. Plasmids expressing P6 mutant were generated by introducing a termination codon or a substitution by polymerase chain reaction (PCR)-based site-directed mutagenesis in pIIIgagCAR plasmid.

FIG. 8 illustates the trans incorporation of Vpr into virus-like particles. COS-7 cells were transfected with pIIIgagCAR plasmid (lane 1), or ptrENV plasmid (lane 2) or cotransfected with both constructs (lane 3). ptrENV was cotransfected with pIIIgagCAR based construct harboring a substitution or a premature termination codon in the p6 protein: L1/stop (lane 4), S17/stop (lane 5), Y36/stop (lane 6), P10,11L (lane 7), L44/stop (lane 8), P49/stop (lane 9). 48 h posttransfection [$^{35}$S]methionine- and [$^3$H]leucine-labelled viral proteins were immunoprecipitated, from the cell lysates or the cell-free supernatant centrifuged through a 20% sucrose cushion, with the HIV-1 positive human serum 162 mixed with a rabbit anti-Vpr polyclonal antibodies and analysed by SDS-PAGE and autoradiography.

The 14 kDa vpr product can be detected in the pelleted virions produced by cells cotransfected with pIIIgagCAR and ptrENV or the P49/stop or P10,11L mutants (FIG. 8, right panel, lanes 3, 9 and 7, respectively). However, virions produced from cells cotransfected in the presence of ptrENV and L1/stop, S17/stop, Y36/stop or L44/stop constructs lacked detectable Vpr (lanes 4, 5, 6 and 8, respectively). These results indicate a direct correlation between the absence of p6 and the loss of Vpr incorporation, suggesting that p6 is directly implicated. Moreover, deletion analysis suggests that the carboxyl terminal of p6 is important for Vpr incorporation indeed, a very short region corresponding to amino acids 45 to 48 inclusively (FGND) is critical for Vpr incorporation. It has already been mentioned that Vpr and Vpx share strong regions of homology. Strikingly, the region of highest homology is found in the region of Vpr which has been shown to interact with p55Gag. This region which is predicted to form an alpha helical structure is thought to be the packaging region of Vpr/Vpx.

Once known, these incorporation domains can be used in a variety of ways. For example, fusion proteins thereof can be inserted in expression vectors according to standard procedures. Such vectors contain all the necessary regulatory signals to promote expression of the fusion protein of interest. Typically, expression vectors are prokaryote specific or eukaryote specific although shuttle vectors are also widely available.

Prokaryotic expression are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

For administration to humans, the prescribing medical professional will ultimately determine the appropriate dosage for a given patient, and this can be expected to vary according to the chosen therapeutic regimen (i.e DNA construct, protein, cells), the response and condition of the patient as well as the severity of the disease.

The present invention will be more readily understood by referring to the following examples which are given to illustrate the invention rather than to limit its scope.

EXAMPLE I

Incorporation of a Specific Epitope into Retroviral Particles from a HIV-1 Cloned Provirus (cis incorporation)

The ability of a foreign antigen to be incorporated when expressed in cis (with respect to the viral genome) into viral particles when fused to Vpr protein was examined. Trans-incorporation (trans with respect to the viral genome) of Vpr chimeric proteins into Vpr-virion in MT4 cells presents limitations due to the low transfection efficiency-obtained when two expression vectors are transfected in T cell lines. To overcome these limitations, a construct expressing a Vpr chimeric protein was designed. A Vpr-Vpu fusion protein was cloned into a Vpu-minus HIV-1 provirus plasmid (pHxBRU; Lavallée et al., 1994, J. Virol., 68:1926–1934), the fusion protein (VprIE) contains the first 88 amino acids of Vpr from the LAI strain and a Vpu epitope (FIG. 9). The last 18 C-terminal amino acids of Vpu which contains a specific epitope (Cohen et al., 1988, Nature, 334:532–534) has been cloned into a XbaI-created restriction site located at the 3' end of the Vpr sequence, at position 5410 on the pHxBRU genome to yield pHxBRU-VprIE. The Vpu epitope is recognized by the specific Rabbit anti-Vpu peptide serum described by (Cohen et al., 1988, Nature, 334:532–534). The pHxBRU-VprIE construct was transfected in MT4 cells and the incorporation of the Vpr-Vpu fusion protein into virions was measured.

Two million MT4 cells were transfected with the pHx-BRU VprIE provirus. 48 h post-transfection, cells were labelled with 100 $\mu$Ci of $^{35}$S-methionine and 100 $\mu$Ci of $^3$H leucine for 16 h. Virions were pelleted from the cell-free supernatants by ultracentrifugation at 35,000 rpm through a 20% sucrose cushion for 2 h. Both cells and sucrose cushion pelleted viruses were lyzed in RIPA buffer (140 mM NaCl, 8 mM NaHPO$_4$, 2 mM NaH$_2$PO$_4$, 1% Nonidet™ P-40, 0.5% sodium deoxycholate, 0.05% SDS) and immunoprecipitated with a HIV-1 positive human serum combined with a rabbit anti-Vpr serum or with a rabbit anti-Vpu serum. Analysis of vpr products in the cell lysates and supernatants has revealed that 1) Vpr-Vpu chimeras are stably expressed in transfected cells and 2) both Vpu ($\alpha$Vpu) and Vpr ($\alpha$Vpr) antisera are able to immunoprecipitate the chimeric product from the virions. These data indicate that the Vpu epitope was successfully transferred into virions when expressed as a Vpr fusion product.

EXAMPLE II

Expression of Vpr Chimeras in trans from Retroviral Vectors

Since one purpose of the present invention is to provide a therapeutic and/or prophylactic agent for HIV infections, an in vitro model was developed in order to express a vpr/vpx-chimeric protein in trans with respect to the viral genome. The ability of a foreign antigen to be incorporated in trans into viral particles was examined then with this in vitro model.

A—Construction of Retroviral Vectors Encoding Vpr Fusion Proteins

Chimeric molecules were developed by fusion of Vpr sequences with either sequences encoding different enzymatic activities or random amino acid sequences of different lengths. In addition to the already described VprIE (FIG. 9), Vpr was fused to the prokaryotic gene chloramphenicol acetyl-transferase (CAT), to generate VprCAT (FIG. 9). To generate stable CD4$^+$ T cell lines expressing constitutively Vpr-based chimeric proteins, retroviral vector technology was used. Since an important feature in any gene therapy approach is the method by which foreign DNA is introduced into cells, the method used to transduce a desired gene inside the cells must be accurately chosen. Retroviral vectors are preferred vectors for gene transfer of mammalian cells in culture, because they lead to high efficiency transformation of mammalian cells through stable integration of proviral DNA into transcriptionally active regions of cellular genome. These vectors contain cis-acting elements [long terminal repeats (LTR), primer binding site (PBS), packaging signal (psi), and polyuridine track], required for viral replication, integration, gene expression and packaging as well as a selectable marker. The transacting proteins (Gag, Pol and Env), required for viral assembly, infection, replication and integration are provided by helper plasmid(s) present in packaging cell lines and are expressed from an RNA lacking a psi signal.

The complete Vpr-CAT and Vpr-IE gene were amplified by PCR with mutagenic BamHI oligonucleotides and inserted into the unique BamHI restriction site of the retroviral vector pBaBepuro, which contains a puromycin resistant gene (FIG. 9; Morgenstern et al., 1990, Nucl. Acids Res. 18: 3587–96). pBaBepuro-VprCAT and pBaBepuro-VprIE were then transfected into the amphotropic Damp packaging cell line. After selection with puromycin, Damp cell lines (Damp-Vpr-CAT and Damp-Vpr-IE) able to produce recombinant retroviruses (Morgan et al., 1993, Annu. Rev. Biochem. 62: 191–217) were generated.

B—Generation of Jurkat CD4+ T Cell Lines Expressing Constitutively the VprCAT and VprIE Proteins The amphotropic murine retroviruses encoding pBaBepuro-VprCAT or pBaBepuro-VprIE (FIG. 9), produced respectively from Damp-VprCAT and Damp-VprIE, were used to transduce CD4$^+$ Jurkat cells (CD4+ T cell lines highly permissive to HIV infection). Following puromycin selection Jurkat-VprCAT and Jurkat-VprIE cell lines were isolated. Briefly, $1,2 \times 10^6$ Damp-VprX, cells were seeded in 100-mm petris dishes for 48 hours. Vpr-X indicates VprIE, VprCAT or any Vpr (or Vpx) chimeric protein. The medium was then removed and replaced by 4 ml of fresh medium. 16 hours later the medium containing a high level of retroviruses was harvested and used to infect $3 \times 10^6$ of centrifuged Jurkat cells. After 48 hours, the transduced Jurkat cells were cultured in fresh medium containing 0,2 ug/ml puromycin for 3 weeks. Jurkat-VprCAT and Jurkat-VprIE resistant cell lines were then isolated and amplified.

C—Expression of Vpr-Based Chimeric Proteins in Jurkat-VprX Cell Lines.

In the stable Jurkat cell line described in (B), the fusion protein derived from pBaBepuro-VprX are driven by the 5' MoMuLV LTR and are expected to be constitutively expressed. To evaluate the expression of the chimeric proteins and to demonstrate that large molecules and functional enzymatic activities can be efficiently transferred to the virion, the CAT activity associated with the virions generated in transduced Jurkat cells was measured. The rapid, sensitive, quantifyable and reproducible assays have been extensively de scribed to measute the activity of CAT (European Patent Application published under No. 474,797 on Mar. 18, 1992 in the name of DANA FARBER CANCER INSTITUTE)

Briefly, $3 \times 10^6$ Jurkat-VprCAT cell were infected with equivalent amounts of HIV-1 Vpr+ or Vpr− virus (pHxBRU and pHxBRU-RATG−, respectively), as evaluated by reverse transcriptase (RT) activity associated with the HIV-1 Vpr+ or Vpr− viral stocks (100 000 CPM), in 1 ml of culture medium for 3 hours and then diluted in 6 ml of medium (Aldovini et al., Eds, 1990, Techniques in HIV research, Stockton Press). pHxBRU-RATG− was generated by introducing a GTG codon instead of the ATG initiation codon in the Vpr gene from the PHxBRU proviral clone (Lavallée et al., 1994, J. Virol., 68:1926–1934). Following viral adsorption, cells were passed every three days. After 20 days, during the peak of viral production, supernatant containing the virus were collected. Virions were then purified by ultracentrifugation through a 20% sucrose cushion (Lavallée et al., 1994, J. Virol., 68:1926–1934). The pelleted virus were resuspended in 80 ul of Tris-HCl 250 mM and lysed by freeze and thaw. 70 ul of the lysed virus was then assayed for CAT activity. Table 1 shows the CAT activity associated with the HIV-1 virions produced in the Jurkat VprCAT transduced cells.

TABLE 1

CAT activity associated to HIV-1 virions produced in a Jurkat-VprCAT transduced cell line

|  | CAT Activity % Acetylation |
| --- | --- |
| Mock | 0,29 |
| Jurkat-VprCAT/pHxBRU | 1,44 |
| Jurkat-VprCAT/pHxBRU-R ATG− | 5,09 |

Detection of CAT activity in the virions thus revealed that 1) the VprCAT chimera is constitutively expressed in transduced Jurkat cells, 2) the fusion protein is incorporated into viral particles following infection and 3) the lower CAT activity detected in virus produced from transduced cells infected with the HIV-1 Vpr+ strain (pHxBRU) suggests a competition for virion incorporation between the wild type Vpr and the VprCAT chimeric protein.

These data indicate that the Vpr fusion protein can be successfully expressed in transduced cells and transferred into virions when expressed in trans from a CD4+ T cell line. In addition the data demostrate that enzymatic activity associatead with the chimeric protein can be targeted into HIV virions. Thus, as shown previously for the Vpr/Vpx chimera expressed from a recombinant HIV provirus, the VprCAT chimera can be incorporated in trans in HIV virions when expressed from a stable cell line.

EXAMPLE III

Vpr-Based Chimeric Proteins and Protection Against HIV Infection

The in vitro model described above, which expresses constitutively Vpr chimeras, was used to test the antiviral activity of these fusion proteins on viral replication.

A—characteization of Jurkat Cell Lines Expressing Vpr Chimeric Proteins

To demonstrate that foreign molecules and functional enzymatic activities can be expressed in CD4+ Jurkat cell lines without affecting cell physiology, cell growth in non-infected Jurkat-VprX cell lines was analyzed. During 5 weeks, growth was monitored by assessing cell viability using the Trypan Blue exclusion method (every three days; Aldovini et al., Eds, 1990, Techniques in HIV research, Stockton Press). All the Jurkat-VprX cell lines were shown to grow at a rate similar to the parental Jurkat cell line (mock-Jurkat TA), as evidenced in FIG. 10, by the virtual super-imposition of the growth rate curves of the parental Jurkat cell line, mock infected, and that of Jurkat-Vpr-IE/pHxBRU-R ATG−.

Figure 10:
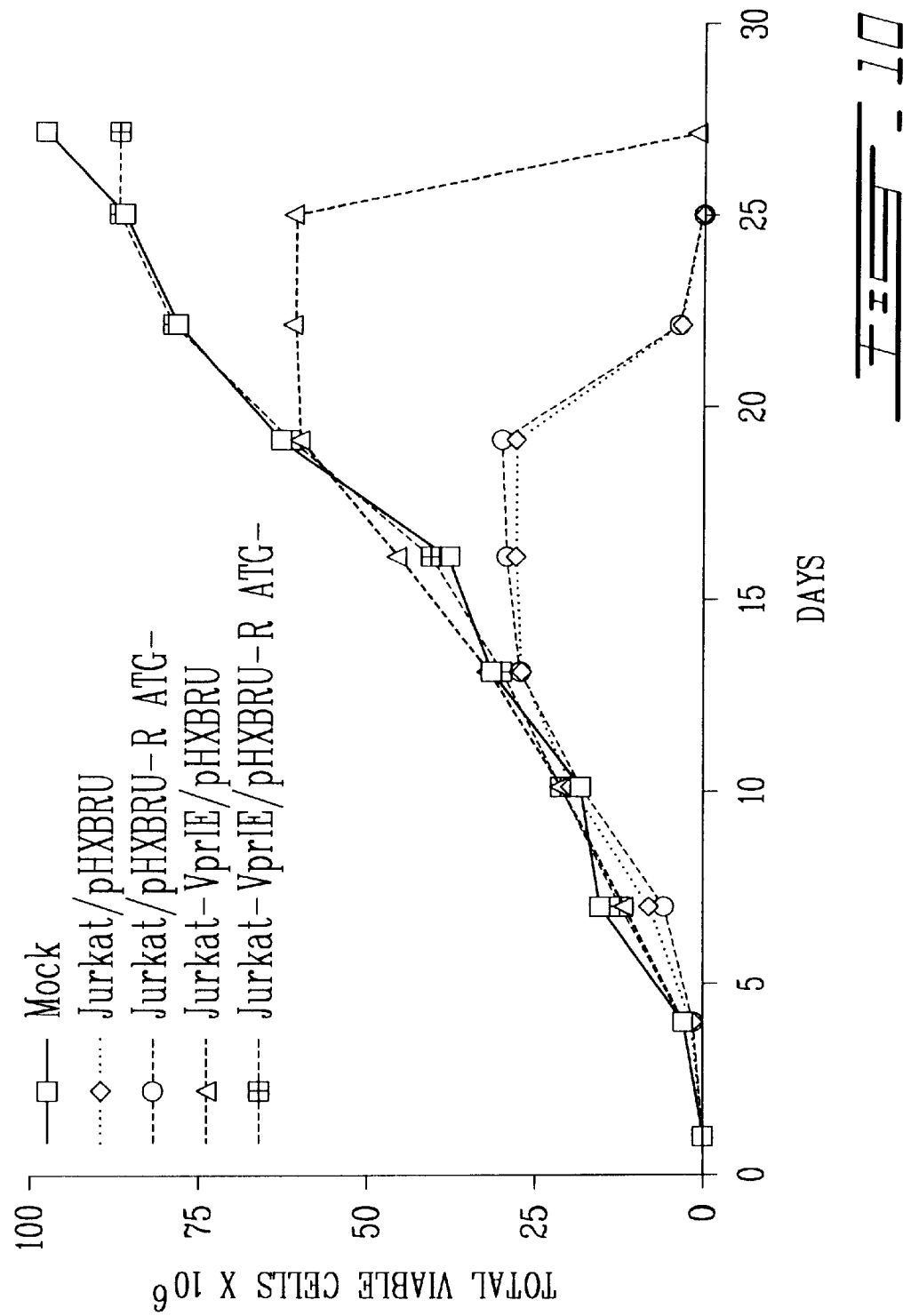
FIG. 10 shows the effect of VprIE (as showed in FIG. 9) expression on the growth rate and viability of Jurkat cells when challenged with HIV (pHxBRU or pHxBRU-R ATG⁻) .
Figure 11:
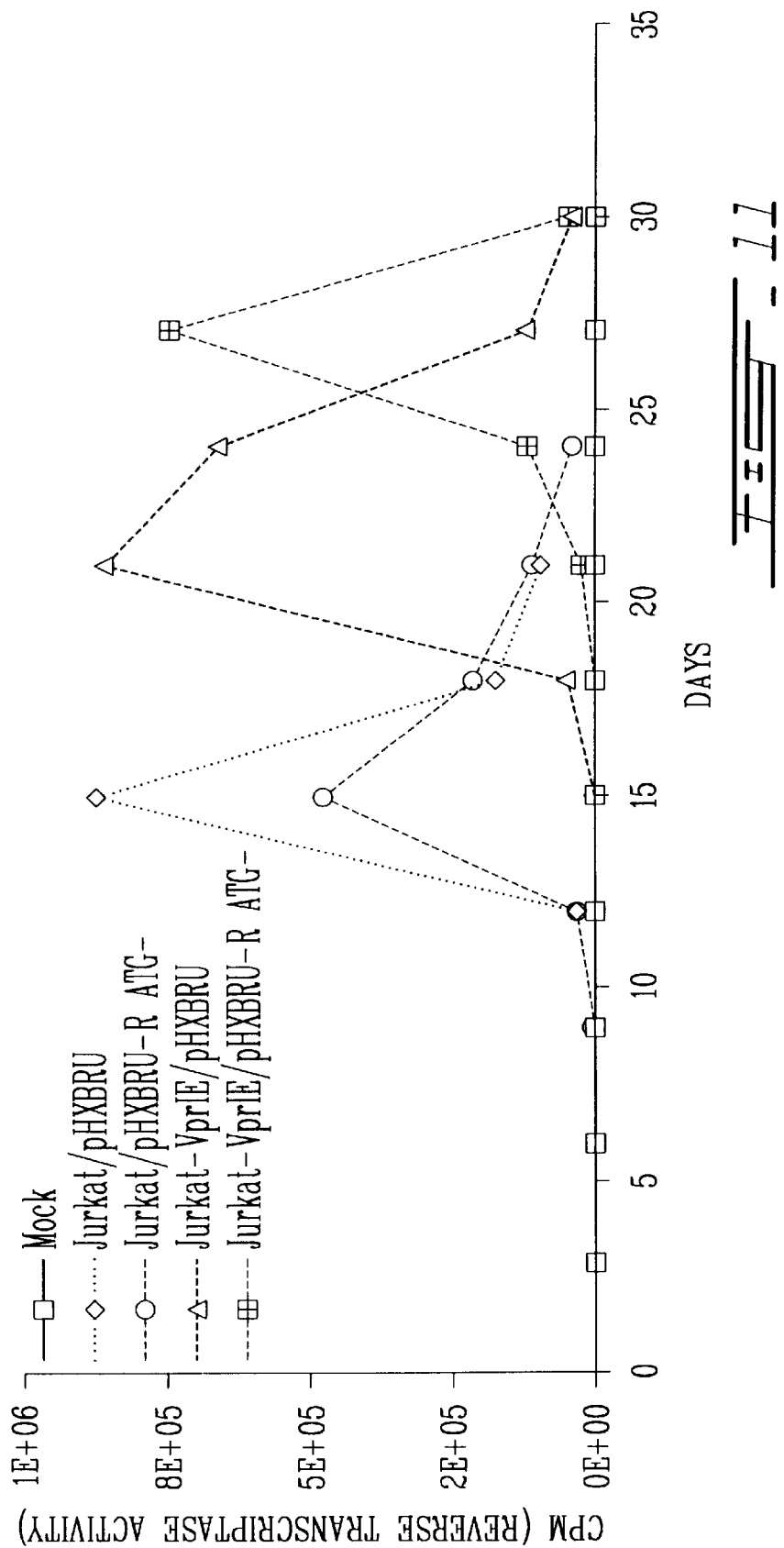
FIG. 11 shows the effects of VprIE expression on HIV-1 replication, in stably transfected Jurkat cells.
Figure 12:
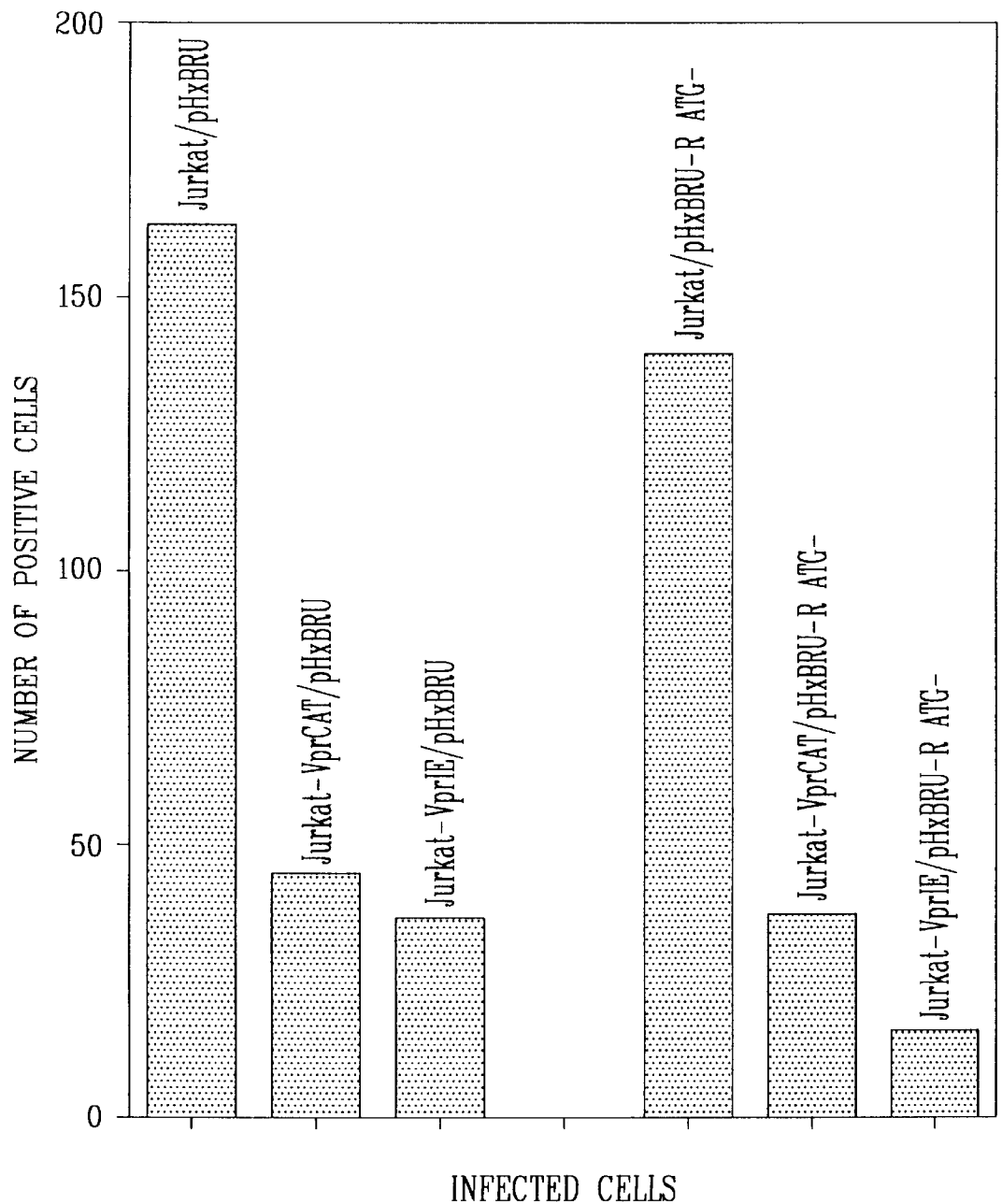
FIG. 12 shows the infectivity potential of HIV virions harboring a Vpr-chimeric protein.

The ability of Vpr fusion proteins to protect CD4+ T cell lines against HIV infection was then evaluated. The Jurkat-VprIE and Jurkat-VprCAT cell lines were challenged with HIV vpr+ and HIV vpr− viruses (pHxBRU and pHxBRU-R ATG−, respectively) to assess their susceptibility to viral infection. The infection kinetic was monitored by measuring viral production (RT activity in the supernatant) and the presence of cytopathic effects (syncytium formation and viable cell counts) every three days during four weeks (Aldovini et al., Eds, 1990, Techniques in HIV research, Stockton Press). Briefly, $3 \times 10^6$ cells of each Jurkat cell lines were infected with a 100 000 CPM RT activity-associated viral stock in 1 ml of medium for 3 hrs and then diluted in 6 ml with culture medium. Every 3 days during one month, RT activities were measured from supernatant aliquots and the number of cells in the cultures was determined by counting, from aliquot therefrom, the number of cells able to exclude trypan blue dye. The cell cultures were diluted to approximately 500,000 cells per ml and 200 ul of supernatant were harvested for R.T. activity detection (Aldovini et al., Eds, 1990, Techniques in HIV research, Stockton Press). The data indicate that all CD4+ T cell lines expressing Vpr chimeric proteins exhibited, albeit to a different extent, a non permissiveness to HIV infection as compared to the highly HIV permissive parental cells (mock-Jurkat TA). FIG. 11 shows that the Jurkat-VprIE exhibited a peak viral production 21 days post-infection when challenged with the HIV-1 vpr+ virus and 27 days post infection when challenged with the HIV-1 vpr− strains. In contrast the parental Jurkat cell line exhibited full viral production 15 days post infection when challenged with either the vpr+ or Vpr− viruses. In addition, viable cell counts demonstrated that Jurkat-VprIE cells had survived HIV-1 infection even after 27 days. Indeed, as previously mentioned the rate of cellular growth was identical to the uninfected parental Jurkat cell control (FIG. 10). In contrast, the infected parental cell culture was completely killed by day 22. (Aldovini et al., Eds, 1990, Techniques in HIV research, Stockton Press).

The data obtained demonstrate that 1) the VprIE fusion protein when provided in trans in Jurkat cells can efficiently delay HIV-1 replication and cytopathic effect such as syncytium formation; and 2) the vprIE chimeric protein was successfully able to protect Jurkat cells from HIV-1 infection for more than 25 days post-infection while allowing normal cell growth.

B—Incorporation of Vpr-Chimeric Protein into HIV Virion Affects Viral Infectivity The assembly and maturation of HIV-1 viral particles is a complex process which involves multiple interactions between viral and cellular constituents. The presence of non-relevant amino acid sequence fused to Vpr during assembly and budding may, due to steric hindrance, affect viral morphogenesis and maturation, thereby resulting in the production of virus with drastically reduced infectious potential. Indeed, as shown above the introduction of 18 amino acids derived from HIV-1 Vpu at the C-terminal end of vpr reduced considerably the replication and spread of HIV in tissue culture. Similar results were also obtained when a larger amino-acid sequence encoding CAT was fused to Vpr and similar results are expected using a Vpx-Vpu fusion or Vpx-X fusion.

To evaluate the infectivity potential of HIV virions that had incorporated the Vpr-CAT or Vpr-IE fusion proteins, Jurkat-VprCAT and Jurkat-VprIE cells were transfected with HIV-1 $vpr^+$ or HIV-1 $vpr^-$ viruses. Briefly, $10\times10^6$ Jurkat or Jurkat-VprX cells were transfected by the DEAE-Dextran method with 10 $\mu$g of HIV-1 $vpr^+$ (pHxBRU) or HIV-1 $vpr^-$ (pHxBRU-R $ATG^-$) infectious molecular clones. After 12 and 24 hr, p24 assay (ELISA) was performed on culture supernatants to evaluate viral production. The level of p24 antigen was similar in all samples indicating that no impairment at the level of gene expression, assembly and release of the viral particles had occurred. These results indicated that the infectivity potential of the released particles that incorporated Vpr-based chimeric molecules may be affected. To evaluate the infectious potential of HIV virions containing Vpr chimeric proteins, a MAGGI assay was performed (Kimpton et al., 1992, J. Virol. 66: 2232–39). Briefly, 35,000 HeLa $CD4^+$ B-gal cells were seeded in 24 plates and infected 24 hr later with 300,000 CPM (by RT) of HIV-1, produced from Jurkat or Jurkat-VprX cells infected with HIV-1 $vpr^+$ or $vpr^+$ strains, respectively. 24 hours post-infection B-galactosidase (B-gal) activity expressed in infected cells was measured. The level of B-gal activity following infection represents a measure of the infectivity of the virus. FIG. 12 shows that HIV-1 containing Vpr chimeric proteins are strongly impaired in their ability to infect $CD4^+$ cells.

Overall the data indicates that 1) gene expression, assembly and release are not affected by the expression of Vpr-chimeric proteins in infected cells; and 2) a 5 to 10-fold decrease in viral infectivity can be measured in viruses that incorporated Vpr-chimeric proteins as compared to wild-type virus.

EXAMPLE IV

Use of Vpr-Protease Chimeric Proteins Against HIV Infections

The examples described above demonstrated that Vpr chimeric proteins are targeted into HIV virions and affect the structural organization and/or functional integrity of the virions.

The following example will illustrate the use of a Vpr-antiviral chimera, such as a Vpr-protease chimera for protecting the cells, in which it is expressed, against HIV infection. Indeed, degradation of the protein content in the virions will lead to completely defective viral particles even though small level of Vpr-protease chimeric molecules are incorporated.

A—Construction of Vpr-Based Chimeric Molecules in which the Vpr Incorporation Domain is Fused to Peptide Sequencs Exhibiting Potential Antiviral Properties Virus-encoded RNA and proteins represent the major components of viral particles. A preferred strategy according to the present invention takes advantage of the experiments that had indicated that functional enzymatic activity can be targeted to the virion as Vpr-based chimeric molocules. Using a similar approach, a sequence encoding a proteolytic activity can be fused to the Vpr C-terminus. It is believed that the presence of such an activity in the virion will lead to the destruction and/or formation of defective viral particles. Proteases are enzymes that catalyze the cleavage of peptide bonds of protein substrates. Many eukaryotic and prokaryotic proteases have been extensively studied and are commercially available as reagents for molecular biology. The selection of appropriate proteases for Vpr-based gene therapy will be preferentially based on the following characteristics: i) the candidate protease has a large spectrum endopeptidase activity: ii) the protease should be functional in the physiological conditions found in the virion; and iii) its molecular weight should not interfere with virion packaging.

Uncontrolled proteolytic activity can destroy the protein component of cells and tissues. One naturally-occurring mechanism for controlling protease activity during biosynthesis is the presence of an amino-terminal extension fused to the enzyme. Proteolytic cleavage of the peptide bond between the so-called propeptide and the enzyme essentially reverses this evolutionary addition and restores enzymatic activity. It is thus a preferred embodiment of the present invention to use the Vpr/Vpx virion incorporation domain as a propeptide and fuse it to the active proteolytic domain of protease. One candidate protease that is considered for fusion to the Vpr/Vpx sequence is a prokaryotic protease such as the calcium-dependent protease of the cyanobacterium Anabaena, or a eukaryotic protease such as the alkaline exoprotease (ALP) of *Aspergillus fumigatus* and Cathepsin G. The advantage of prokaryotic proteases over eukaryotic proteases is that they do not require to go through an intracellular pathway for maturation and proper folding.

The presence of an amino terminal Vpr sequence (or Vpx sequence) in Vpr-protease fusion products (or its Vpx counterpart) can be designed to lead to the formation of inactive enzymatic products during intracellular biosynthesis. However, as one goal is the destruction or impairment of infectious viral particles, the constructs preferably contains a regulatory mechanism that can specifically activate the enzymatic activity of the protease in the virions. The HIV-1 Gag precursor proteolytic processing sites are cleaved specifically and sequentially by the viral protease during virion budding and maturation. When full-length Gag proteins are digested with recombinant HIV-1 protease in vitro, four of the five major processing sites in Gag are cleaved at rates that differ by as much as 400-fold. Proterably, it will introduce an, HIV-1 specific proteage cleavage site sequence, corresponding by exemplar to the p17/p24 processing site (Myers et al., 1993, Human Retroviruses and AIDS 1993 I–II, Los Alamos National Laboratory, New Mexico, USA)), between the Vpr virion incorporation domain and the protease sequences (FIG. 13). Based on the hydrophobic/hydrophilic property and enzymatic cleavage kinetic (Vmax, Ki) of the p17/p24 processing site (intermediate rate of cleavage), this sequence is predicted; i) to be located at the surface of the fusion proteins; and ii) to be digested only within the virions since only there substrate will reach concentrations necessary for efficient proteolysis. During budding and maturation, cleavage of Vpr-protease chimeric protein by the HIV-1 protease will activate the prokaryotic enzymatic activity in the virions. It should be understood that other types of linkers between the Vpr/Vpx sequence and the chosen antiviral sequence are well known and available to the skilled artisan. The presence of such non-specific protease activity in the virion is predicted to lead to the destruction and/or generation of defective viral particles.

B—Structure of the Minigene Encoding Vpr-Based Chimeric Proteins under HIV-1 Tat Regulation During gene therapy, Vpr/Vpx-chimeric proteins can be expressed in trans from a foreign gene integrated in the cell genome. In addition, expression of the Vpr-chimeric proteins will be preferentially restricted to HIV-1 infected cells since: i) long term expression of Vpr/Vpx-chimeras could lead to cellular toxicity; and ii) existing cell-mediated immunity (in patients) could lead to the death of all transformed cells expressing the anti-HTV-1 protein, although not infected by HIV-1.

Selected fusion proteins are preferentially cloned 3' to a constitutive or inducible promoter. The cytomegalovirus (CMV) early gene promoter which is an example of a powerful constitutive promoter. Numerous types of promoters could also be used. To ensure a specific control of the transgene expression, the CMV promoter is preferentially fused to the transactivator (Tat) responsive element (TAR), which in response to HIV-1 Tat binding, mediates an increase of transcription initiation and facilitates mRNA elongation (FIG. 13). Thus full expression of the transgene can be restricted to cells expressing Tat, such as in HIV-1 infected cells C—Construction of Retroviral Vectors that Oppress a Vpr-Based Chimera An important feature in any gene therapy approach is the method by which foreign DNA is introduced into cells. Safe replication-defective retroviral vectors have already been used in experimental clinical trials to deliver and stably integrate therapeutic genes into human cells (Morgan et al., 1993, Annu. Rev. Biochem. 62: 191–217). In a preferred embodiment of the present invention, the gene transfer experiments are carried out by cloning the Tat-inducible minigene encoding the Vpr-based chimeric protein (FIG. 13) into an appropriate Mo-MuLV-derived retroviral vector. A number of these retroviral vectors are readily available and well known in the field of molecular biology and gene therapy. As a control, a retroviral vector containing a frameshift mutation in the Vpr virion incorporation domain can also be generated. According to the well known methods of gene therapy, to produce amphotropic pseudotyped vector particles, the retroviral vector is transfected into the psi CRIP amphotropic packaging call line to generate retroviral vector producer cell lines. Amphotropic pseudotyped retroviral vector particles capable of infecting human cells, can then be tested for: i) their titer using NIH-3T3 and human CD4$^+$lymphocyte-derived CEM-10 (adherent) cell lines; ii) lack of recombinant virus via southern blot analysis; and iii) lack of helper virus production via infection of a mouse cell line. The Vpr-protease chimera will be tested in CD4$^+$ T cell lines or CD4$^+$ peripheral blood lymphocytes (PBL) to evaluate the ability of the fusion protein to protect the cells against HIV infection.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An expression vector comprising:
   (a) nucleic acid segment encoding a recombinant protein for interfering with incorporation of native Vpr and/or native Vpx into HIV-1 or HIV-2 virion, wherein said recombinant protein comprises a Vpr/Vpx virion incorporation domain which includes the predicted N-terminal alpha helix of a viral protein sequence selected from the group consisting of HIV-1 Vpr, HIV-2 Vpr, HIV-2 Vpx, SIV Vpr and SIV Vpx, or the P6 domain of a $Pr55^{gag}$-precursor protein of said HIV-1 or HIV-2 virion and wherein said nucleic acid segment comprises a nucleotide sequence encoding an amino acid sequence selected from the group consisting of SEQ ID NO:1, SEQ ID NO:2, SEQ ID NO:3, SEQ ID NO:4, and SEQ ID NO:5, whereby said recombinant protein when expressed in trans with respect to the HIV-1 or HIV-2 genome, interacts with at least one of a native viral protein selected from the group consisting of a p6 domain of a $Pr55^{gag}$-precursor protein, a Vpr protein, and a Vpx protein, thereby enabling the production of viral particles with a reduced amount of said native Vpr or Vpx protein, while allowing normal cell growth of a cell expressing said recombinant protein; and (b) a promoter operably linked to said nucleic acid segment.

2. An isolated cell of a eukaryote or prokaryote transformed with the expression vector of claim 1.

3. A composition for reducing infectivity of HIV-1 or HIV-2 in vitro, which comprises an effective amount of said expression vector of claim 1 in association with a pharmaceutically acceptable carrier.

4. A composition for targeting into an HIV-1 or HIV-2 virion, which comprises an effective amount of the expression vector of claim 1, in association with a pharmaceutically acceptable carrier.

5. The expression vector of claim 1, wherein said nucleic acid segment comprises a nucleotide sequence encoding the amino acid sequence selected from the group consisting of SEQ ID NO:1, SEQ ID NO:2, and SEQ ID NO:4.

6. The expression vector of claim 5, wherein said nucleic acid segment comprises a nucleotide sequence encoding the amino acid sequence of amino acids 1 to 93 of SEQ ID NO:1.

7. The expression vector of claim 5, wherein said nucleic acid segment comprises a nucleotide sequence encoding the amino acid sequence as set forth in SEQ ID NO:4.

8. The expression vector of claim 1, wherein said recombinant protein comprises the p6 domain of $Pr55^{gag}$ precursor protein of said HIV-1 or HIV-2 virion.

9. A composition for reducing infectivity of HIV-1 or HIV-2, which comprises an effective amount of said expression vector of claim 1 in association with a pharmaceutically acceptable carrier.

10. The expression vector of claim 8, wherein said p6 domain of $Pr55^{gag}$ has the amino acid sequence set forth in SEQ ID NO:5.

11. An expression vector comprising:

(a) a nucleic acid segment encoding a recombinant protein for interfering with incorporation of native Vpr and/or native Vpx into HIV-1 or HIV-2 virion, wherein said recombinant protein comprises a Vpr/Vpx virion incorporation domain having a nucleic acid sequence which encodes an amino acid sequence selected from the group consisting of:

i) amino acids 1–72 of SEQ ID NO:1 of HIV-1 Vpr;

ii) amino acids 1–88 of SEQ ID NO:1 of HIV-1 Vpr; and iii) amino acids 1–93 of SEQ ID NO:1 of HIV-1 Vpr, or the p6 domain of a $Pr55^{gag}$-precursor protein of said HIV-1 or HIV-2 virion whereby said recombinant protein when expressed in trans with respect to the HIV-1 or HIV-2 genome, interacts with at least one of a native viral protein selected from the group consisting of a p6 domain of a $Pr55^{gag}$-precursor protein, a Vpr protein, and a Vpx protein, thereby enabling the production of viral particles with a reduced amount of said native Vpr or Vpx protein, while allowing normal cell growth of a cell expressing said recombinant protein; and (b) a promoter operably linked to said nucleic acid segment.

12. The expression vector of claim 11, wherein said amino acid sequence is selected from the group consisting of:

i) amino acids 1–72 of SEQ ID NO:1 of HIV-1 Vpr; and ii) amino acids 1–88 of SEQ ID NO:1 of HIV-1 Vpr.

13. A composition for reducing infectivity of HIV-1 or HIV-2, which comprises an effective amount of said expression vector of claim 11 in association with a pharmaceutically acceptable carrier.

14. A composition for reducing infectivity of HIV-1 or HIV-2, which comprises an effective amount of said expression vector of claim 12 in association with a pharmaceutically acceptable carrier.

15. An isolated cell of a eukaryote or prokaryote transformed with the expression vector of claim 11.

16. An isolated cell of a eukaryote or prokaryote transformed with the expression vector of claim 12.

17. A composition for reducing infectivity of HIV-1 or HIV-2 in vitro, which comprises an effective amount of said expression vector of claim 11 in association with a pharmaceutically acceptable carrier.

18. A composition for reducing infectivity of HIV-1 or HIV-2 in vitro, which comprises an effective amount of said expression vector of claim 12 in association with a pharmaceutically acceptable carrier.

19. An expression vector comprising:

(a) a nucleic acid segment encoding a chimeric protein that is incorporated into an HIV-1 or HIV-2 virion when expressed in trans with respect to the HIV-1 or HIV-2 genome comprising a first and a second portion, wherein said first portion comprises a Vpr/Vpx incorporation domain, said first portion consisting of a nucleic acid sequence which encodes an amino acid sequence selected from the group consisting of amino acids 1 to 88 of HIV-1 Vpr, SEQ ID NO:1, and amino acids 1 to 72 of HIV-1 Vpr, SEQ ID NO:1; and wherein said Vpr/Vpx virion incorporation domain interacts with the p6 domain of $Pr55^{gag}$, thereby enabling incorporation of said chimeric protein into said HIV-1 or HIV-2 virion; and (b) a promoter operably linked to said nucleic acid segment.

20. A composition for reducing infectivity of HIV-1 or HIV-2, which comprises an effective amount of said expression vector of claim 19 in association with a pharmaceutically acceptable carrier.

21. An expression vector comprising:

(a) a nucleic acid segment encoding a chimeric protein that is incorporated into an HIV-1 or HIV-2 virion when expressed in trans with respect to the HIV-1 or HIV-2 genome, comprising a first and a second portion, with said second portion being fused to the C-terminal portion of said first portion, wherein said first portion has a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr, and SIV Vpx; and wherein said Vpr/Vpx virion incorporation domain interacts with the p6 domain of $Pr55^{gag}$, thereby enabling incorporation of said chimeric protein into said HIV-1 or HIV-2 virion; and (b) a promoter operably linked to said nucleic acid segment.

22. The expression vector of claim 21, wherein said first portion comprises a nucleotide sequence encoding an amino acid sequence that is selected from the group consisting of SEQ ID NO:1, SEQ ID NO:2, SEQ ID NO:3, and SEQ ID NO:4.

23. The expression vector of claim 22, wherein said first portion comprises a nucleotide sequence encoding an amino acid sequence spanning amino acids 1 to 88 of SEQ ID NO:1.

24. The expression vector of claim 22, wherein said first portion comprises a nucleotide sequence encoding an amino acid sequence as set forth in SEQ ID NO:4.

25. The expression vector of claim 24, wherein said second portion possesses antiviral activity.

26. The expression vector of claim 25, wherein a first nucleic acid sequence encodes said first portion and a second nucleic acid sequence encodes said second portion, and wherein said antiviral activity is encoded by a protein domain which is fused to said first portion through a linker nucleic acid segment encoding a HIV-specific protease cleavage site, said linker nucleic acid fusing said first and second nucleic acid sequences.

27. The expression vector of claim 26, further comprising a transactivator responsive element TAR, upstream of said nucleic acid segment encoding said chimeric protein.

28. A composition for reducing infectivity of HIV-1 or HIV-2, which comprises an effective amount of said expression vector of claim 26 in association with a pharmaceutically acceptable carrier.

29. The expression vector of claim 22, wherein said first portion comprises a nucleotide sequence encoding an amino acid sequence spanning amino acids 1 to 93 of SEQ ID NO:1.

30. The expression vector of claim 21, wherein said chimeric protein allows normal cell growth of a cell expressing said chimeric protein.

31. A composition for targeting into an HIV-1 or HIV-2 virion, which comprises an effective amount of the expression vector of claim 30, in association with a pharmaceutically acceptable carrier.

32. The expression vector of claim 21, wherein said viral protein is selected from the group consisting of HIV-1 Vpr, HIV-2 Vpr and SIV Vpr.

33. A composition for reducing infectivity of HIV-1 or HIV-2, which comprises an effective amount of said expression vector of claim 32 in association with a pharmaceutically acceptable carrier.

34. The expression vector of claim 32, wherein said first portion comprises a neuclotide sequence encoding an amino acid sequence that is selected from the group consisting of SEQ ID NO:1, SEQ ID NO:2, and SEQ ID NO:4.

35. A composition for reducing infectivity of HIV-1 or HIV-2, which comprises an effective amount of said expression vector of claim 34 in association with a pharmaceutically acceptable carrier.

36. The expression vector of claim 32, wherein said viral protein is HIV-1 Vpr.

37. The expression vector of claim 36, wherein said second portion comprises an amino acid sequence having RNAse or protease activity, whereby said RNAse or protease activity induces the degradation of RNA or protein inside said HIV-1 or HIV-2 virion.

38. The expression vector of claim 36, wherein said second portion prevents proper virion morphogenesis of said HIV-1 or HIV-2 virions.

39. The expression vector of claim 36, wherein said first portion comprises a nucleotide sequence encoding the amino acid sequence of amino acids 1 to 93 of SEQ ID NO:1.

40. The expression vector of claim 36, wherein said first portion comprises a nucleotide sequence encoding the amino acid sequence as set forth in SEQ ID NO:4.

41. A composition for targeting into an HIV-1 or HIV-2 virion, which comprises an effective amount of the expression vector of claim 36, in association with a pharmaceutically acceptable carrier.

42. The expression vector of claim 21, wherein said second portion comprises a nucleotide sequence encoding an amino acid sequence having RNAse or protease activity, whereby said RNAse or protease activity induces the degradation of RNA or protein inside said HIV-1 or HIV-2 virion.

43. The expression vector of claim 42, wherein a first nucleic acid sequence encodes said first portion and a second nucleic acid sequence encodes said second portion, and wherein said protease activity is encoded by a protease domain which is fused to said first portion through a linker nucleic acid segment encoding a HIV-specific protease cleavage site, said linker nucleic acid fusing said first and second nucleic acid sequences.

44. A composition for reducing infectivity of HIV-1 or HIV-2, which comprises an effective amount of said expression vector of claim 43 in association with a pharmaceutically acceptable carrier.

45. The expression vector of claim 43, further comprising the transactivator responsive element TAR, upstream of said nucleic acid segment encoding said chimeric protein.

46. A composition for reducing infectivity of HIV-1 or HIV-2 in vitro, which comprises an effective amount of said expression vector of claim 21 in association with a pharmaceutically acceptable carrier.

47. The expression vector of claim 21, wherein said viral protein is selected from the group consisting of HIV-2 Vpx, and SIV Vpx.

48. The expression vector of claim 47, wherein said viral protein is HIV-2 Vpx and wherein said first portion comprises a nucleotide sequence encoding the amino acid sequence of SEQ ID NO:3.

49. The expression vector of claim 21, wherein said vector is adapted for expression of said chimeric protein in prokaryotic cells.

50. The expression vector of claim 21, wherein said vector is adapted for expression of said chimeric protein in eukaryotic cells.

51. The expression vector of claim 21, wherein said second portion interferes with molecular interactions necessary for formation or infectivity of said HIV-1 or HIV-2 virion.

52. The expression vector of claim 21, wherein said second portion prevents proper virion morphogenesis of said HIV-1 or HIV-2 virion.

53. An isolated cell of a eukaryote or prokaryote transformed with the expression vector of claim 21.

54. The expression vector of claim 21, wherein a first nucleic acid sequence encodes said first portion and a second nucleic acid sequence encodes said second portion, and wherein said second portion is fused to said first portion through a polypeptide segment encoding a HIV-specific protease cleavage site which is encoded by a linker nucleic acid segment, with said linker nucleic acid fusing said first and second nucleic acid sequences.

55. An isolated cell of a eukaryote or prokaryote transformed with the expression vector of claim 54.

56. The expression vector of claim 54, further comprising the transactivator response element TAR, upstream of said nucleic acid segment encoding said chimeric protein.

57. A composition for targeting into an HIV-1 or HIV-2 virion, which comprises an effective amount of the expression vector of claim 54, in association with a pharmaceutically acceptable carrier.

58. A composition for targeting into an HIV-1 or HIV-2 virion, which comprises an effective amount of the expression vector of claim 21, in association with a pharmaceutically acceptable carrier.

59. A composition for reducing infectivity of HIV-1 or HIV-2, which comprises an effective amount of said expression vector of claim 21 in association with a pharmaceutically acceptable carrier.

60. An expression vector comprising:
(a) a nucleic acid segment encoding a chimeric protein that is incorporated into an HIV-1 or HIV-2 virion when expressed in trans with respect to the HIV-1 or HIV-2 genome comprising a first and a second portion, wherein said first portion has a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr, and SIV Vpx; and wherein said Vpr/Vpx virion incorporation domain interacts with the p6 domain of Pr55$^{gag}$, thereby enabling incorporation of said chimeric protein into said HIV-1 or HIV-2 virion, and wherein said second portion interferes with molecular interactions necessary for formation or infectivity of said HIV-1 or HIV-2 virion; and (b) a promoter operably linked to said nucleic acid segment.

61. The expression vector of claim 60, wherein said viral protein is selected from the group consisting of HIV-1 Vpr, HIV-2 Vpr and SIV Vpr.

62. The expression vector of claim 61, wherein said viral protein is HIV-1 Vpr.

63. An expression vector comprising:

(a) a nucleic acid segment encoding a chimeric protein that is incorporated into an HIV-1 or HIV-2 virion when expressed in trans with respect to the HIV-1 or HIV-2 genome comprising a first and a second portion, said second portion being fused to said first portion through a polypeptide segment encoding a HIV-specific protease cleavage site which is encoded by a linker nucleic acid segment which fuses said first and second nucleic acid sequences, wherein said first portion has a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr, and SIV Vpx; and wherein said Vpr/Vpx virion incorporation domain interacts with the p6 domain of Pr55$^{gag}$, thereby enabling incorporation of said chimeric protein into said HIV-1 or HIV-2 virion; and (b) a promoter operably linked to said nucleic acid segment.

64. The expression vector of claim 63, wherein said viral protein is selected from the group consisting of HIV-1 Vpr, HIV-2 Vpr and SIV Vpr.

65. The expression vector of claim 64, wherein said viral protein is HIV-1 Vpr.

66. A composition for targeting into an HIV-1 or HIV-2 virion, which comprises an effective amount of the expression vector of claim 64, in association with a pharmaceutically acceptable carrier.

67. A composition for targeting into an HIV-1 or HIV-2 virion, which comprises an effective amount of the expression vector of claim 65, in association with a pharmaceutically acceptable carrier.

68. A composition for reducing infectivity of HIV-1 or HIV-2, which comprises an effective amount of said expression vector of claim 63 in association with a pharmaceutically acceptable carrier.

69. An isolated cell of a eukaryote or prokaryote transformed with the expression vector of claim 63.

70. A composition for reducing infectivity of HIV-1 or HIV-2 in vitro, which comprises an effective amount of said expression vector of claim 63 in association with a pharmaceutically acceptable carrier.

71. A composition for targeting into an HIV-1 or HIV-2 virion, which comprises an effective amount of the expression vector of claim 63, in association with a pharmaceutically acceptable carrier.

72. The expression vector of claim 21, further comprising the transactivator response element TAR, upstream of said nucleic acid segment encoding said chimeric protein.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 96 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:1:

Met Glu Gln Ala Pro Glu Asp Gln Gly Pro Gln Arg Glu Pro His Asn
1          5                   10               15

Glu Trp Thr Leu Glu Leu Leu Glu Glu Leu Lys Asn Glu Ala Val Arg
        20                 25                30

```
His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Gln Gln Arg Arg Ala Arg Asn Gly Ala Ser Arg Ser
                85                  90                  95
```

(2) INFORMATION FOR SEQ ID NO:2:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:2:

```
Met Ala Glu Ala Pro Thr Glu Leu Pro Pro Val Asp Gly Thr Pro Leu
1                   5                   10                  15

Arg Glu Pro Gly Asp Glu Trp Ile Ile Glu Ile Leu Arg Glu Ile Lys
                20                  25                  30

Glu Glu Ala Leu Lys His Phe Asp Pro Arg Leu Leu Ile Ala Leu Gly
            35                  40                  45

Lys Tyr Ile Tyr Thr Arg His Gly Asp Thr Leu Glu Gly Ala Arg Glu
    50                  55                  60

Leu Ile Lys Val Leu Gln Arg Ala Leu Phe Thr His Phe Arg Ala Gly
65                  70                  75                  80

Cys Gly His Ser Arg Ile Gly Gln Thr Arg Gly Gly Asn Pro Leu Ser
                85                  90                  95

Ala Ile Pro Thr Pro Arg Asn Met Gln
            100                 105
```

(2) INFORMATION FOR SEQ ID NO:3:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:3:

```
Met Thr Asp Pro Arg Glu Thr Val Pro Pro Gly Asn Ser Gly Glu Glu
1                   5                   10                  15

Thr Ile Gly Glu Ala Phe Ala Trp Leu Asn Arg Thr Val Glu Ala Ile
                20                  25                  30

Asn Arg Glu Ala Val Asn His Leu Pro Arg Glu Leu Ile Phe Gln Val
            35                  40                  45

Trp Gln Arg Ser Trp Arg Tyr Trp His Asp Glu Gln Gly Met Ser Glu
    50                  55                  60

Ser Tyr Thr Lys Tyr Arg Tyr Leu Cys Ile Ile Gln Lys Ala Val Tyr
65                  70                  75                  80

Met His Val Arg Lys Gly Cys Thr Cys Leu Gly Arg Gly His Gly Pro
```

85                  90                      95
Gly Gly Trp Arg Pro Gly Pro Pro Pro Pro Pro Pro Gly Leu Val
                100                 105                 110

(2) INFORMATION FOR SEQ ID NO:4:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:4:

Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
                20                  25                  30

His Phe Pro Arg Ile Trp Leu His Gly Leu Gly Gln His Ile Tyr Glu
            35                  40                  45

Thr Tyr Gly Asp Thr Trp Ala Gly Val Glu Ala Ile Ile Arg Ile Leu
    50                  55                  60

Gln Gln Leu Leu Phe Ile His Phe
65                  70

(2) INFORMATION FOR SEQ ID NO:5:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

Leu Gln Arg Ser Pro Glu Pro Thr Ala Pro Pro Glu Glu Ser Phe Arg
1               5                   10                  15

Ser Gly Val Glu Thr Thr Thr Pro Pro Gln Lys Gln Glu Pro Ile Asp
                20                  25                  30

Lys Glu Leu Tyr Pro Leu Thr Ser Leu Arg Ser Leu Phe Gly Asn Asp
            35                  40                  45

Pro Ser Ser Gln
    50